(12) United States Patent
Joseph et al.

(10) Patent No.: US 9,909,171 B2
(45) Date of Patent: *Mar. 6, 2018

(54) THERMO-CONTROLLABLE HIGH-DENSITY CHIPS FOR MULTIPLEX ANALYSES

(71) Applicant: Takara Bio USA, Inc., Mountain View, CA (US)

(72) Inventors: Victor Joseph, Fremont, CA (US); Amjad Huda, Fremont, CA (US); Alnoor Shivji, Fremont, CA (US); Jie Zhou, Mason, OH (US)

(73) Assignee: Takara Bio USA, Inc., Mountain View, CA (US)

( * ) Notice: Subject to any disclaimer, the term of this patent is extended or adjusted under 35 U.S.C. 154(b) by 113 days.

This patent is subject to a terminal disclaimer.

(21) Appl. No.: 14/857,379

(22) Filed: Sep. 17, 2015

(65) Prior Publication Data

US 2016/0138082 A1 May 19, 2016

Related U.S. Application Data

(63) Continuation of application No. 11/137,305, filed on May 24, 2005, now abandoned, which is a
(Continued)

(51) Int. Cl.
*C12Q 1/68* (2006.01)
*B01L 3/00* (2006.01)
(Continued)

(52) U.S. Cl.
CPC .......... *C12Q 1/686* (2013.01); *B01L 3/50851* (2013.01); *B01L 3/50853* (2013.01);
(Continued)

(58) Field of Classification Search
CPC .... C12M 41/14; C12M 23/48; C12M 1/3446; C12M 23/12; B01L 7/52; B01L 7/00;
(Continued)

(56) References Cited

U.S. PATENT DOCUMENTS 4,683,195 A 7/1987 Mullis et al.
4,683,202 A 7/1987 Mullis
(Continued)

FOREIGN PATENT DOCUMENTS

EP  0438883  5/1996
EP  0637999 B1  12/1998
(Continued)

OTHER PUBLICATIONS

Agrawal, S. ed. Methods in Molecular Biology, "Protocols of Oligonucleotides and Analogs," vol. 20, 1993, Cover Pages and Table of Contents, pp. i-xiv (12 pages).
(Continued)

*Primary Examiner* — Michael Hobbs
(74) *Attorney, Agent, or Firm* — Bret E. Field; Bozicevic, Field & Francis LLP

(57) ABSTRACT

The present invention provides miniaturized instruments for conducting chemical reactions where control of the reaction temperature is desired or required. Specifically, this invention provides chips and optical systems for performing and monitoring temperature-dependent chemical reactions. The apparatus and methods embodied in the present invention are particularly useful for high-throughput and low-cost amplification of nucleic acids.

6 Claims, 27 Drawing Sheets

Related U.S. Application Data continuation-in-part of application No. 10/857,552, filed on May 28, 2004, now abandoned.

(60) Provisional application No. 60/630,789, filed on Nov. 24, 2004.

(51) Int. Cl.

| | |
|---|---|
| *B01L 7/00* | (2006.01) |
| *B82Y 30/00* | (2011.01) |
| *G01N 21/03* | (2006.01) |
| *G01N 35/00* | (2006.01) |
| *G01N 21/01* | (2006.01) |
| *H01L 27/144* | (2006.01) |
| *H01L 31/0203* | (2014.01) |
| *H01L 31/0232* | (2014.01) |
| *H01L 31/024* | (2014.01) |
| *H01L 31/105* | (2006.01) |
| *H01L 31/18* | (2006.01) |
| *G01N 21/64* | (2006.01) |
| *G01N 21/76* | (2006.01) |
| *G01N 35/04* | (2006.01) |

(52) U.S. Cl.
CPC ............... *B01L 7/52* (2013.01); *B82Y 30/00* (2013.01); *C12Q 1/6806* (2013.01); *C12Q 1/6844* (2013.01); *G01N 21/01* (2013.01); *G01N 21/0332* (2013.01); *G01N 21/6452* (2013.01); *G01N 35/0099* (2013.01); *H01L 27/1443* (2013.01); *H01L 31/0203* (2013.01); *H01L 31/024* (2013.01); *H01L 31/02325* (2013.01); *H01L 31/105* (2013.01); *H01L 31/18* (2013.01); *B01L 7/54* (2013.01); *B01L 2200/0689* (2013.01); *B01L 2300/044* (2013.01); *B01L 2300/0636* (2013.01); *B01L 2300/0654* (2013.01); *B01L 2300/0819* (2013.01); *B01L 2300/0829* (2013.01); *B01L 2300/18* (2013.01); *B01L 2300/1822* (2013.01); *B01L 2300/1827* (2013.01); *G01N 21/6408* (2013.01); *G01N 21/76* (2013.01); *G01N 2021/6417* (2013.01); *G01N 2021/6484* (2013.01); *G01N 2035/0405* (2013.01); *G01N 2201/0231* (2013.01)

(58) Field of Classification Search
CPC ........... B01L 2300/0829; B01L 3/5085; B01L 3/5025; B01L 2200/025; G01N 21/6428; G01N 21/6452; G01N 21/253; C12Q 1/04
See application file for complete search history.

(56) References Cited

U.S. PATENT DOCUMENTS

| | | |
|---|---|---|
| 5,210,015 A | 5/1993 | Gelfand et al. |
| 5,252,294 A | 10/1993 | Kroy et al. |
| 5,281,516 A | 1/1994 | Stapleton et al. |
| 5,338,671 A | 8/1994 | Scalice et al. |
| 5,342,581 A | 8/1994 | Sanadi |
| 5,475,610 A | 12/1995 | Atwood et al. |
| 5,494,810 A | 2/1996 | Barany et al. |
| 5,496,517 A | 3/1996 | Pfost et al. |
| 5,498,392 A | 3/1996 | Wilding et al. |
| 5,525,300 A | 6/1996 | Danssaert et al. |
| 5,552,321 A | 9/1996 | Focht |
| 5,552,580 A | 9/1996 | Pfost et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,602,756 A | 2/1997 | Atwood et al. |
| 5,639,423 A | 6/1997 | Northrup et al. |
| 5,656,493 A | 8/1997 | Mullis et al. |
| 5,674,743 A | 10/1997 | Ulmer |
| 5,716,842 A | 2/1998 | Baier et al. |
| 5,720,923 A | 2/1998 | Haff et al. |
| 5,721,136 A | 2/1998 | Finney et al. |
| 5,773,258 A | 6/1998 | Birch et al. |
| 5,779,977 A | 7/1998 | Haff et al. |
| 5,779,981 A | 7/1998 | Danssaert et al. |
| 5,827,480 A | 10/1998 | Haff et al. |
| 5,866,345 A | 2/1999 | Wilding et al. |
| 5,939,312 A | 8/1999 | Baier et al. |
| 5,955,029 A | 9/1999 | Wilding et al. |
| 5,985,555 A | 11/1999 | Bertling |
| 6,015,674 A | 1/2000 | Woudenberg et al. |
| 6,033,880 A | 3/2000 | Haff et al. |
| 6,054,263 A | 4/2000 | Danssaert et al. |
| 6,126,804 A | 10/2000 | Andresen |
| 6,132,580 A | 10/2000 | Mathies et al. |
| 6,153,426 A | 11/2000 | Heimberg |
| 6,174,675 B1 | 1/2001 | Chow et al. |
| 6,184,029 B1 | 2/2001 | Wilding et al. |
| 6,197,572 B1 | 3/2001 | Schneebeli |
| 6,284,525 B1 | 9/2001 | Mathies et al. |
| 6,303,343 B1 | 10/2001 | Kopf-sill |
| 6,306,590 B1 | 10/2001 | Mehta et al. |
| 6,309,886 B1 | 10/2001 | Ambrose et al. |
| 6,337,435 B1 | 1/2002 | Chu et al. |
| 6,406,893 B1 | 6/2002 | Knapp et al. |
| 6,420,143 B1 | 7/2002 | Kopf-sill |
| 6,423,536 B1 | 7/2002 | Javanovich et al. |
| 6,423,948 B1 | 7/2002 | Kwasnoski et al. |
| 6,432,695 B1 | 8/2002 | Zou et al. |
| 6,444,461 B1 | 9/2002 | Knapp et al. |
| 6,448,066 B1 | 9/2002 | Wheatcroft |
| 6,503,750 B1 | 1/2003 | Benett et al. |
| 6,509,186 B1 | 1/2003 | Zou et al. |
| 6,524,532 B1 | 2/2003 | Northrup et al. |
| 6,524,830 B2 | 2/2003 | Kopf-sill |
| 6,537,799 B2 | 3/2003 | Chow et al. |
| 6,541,274 B2 | 4/2003 | Nagle et al. |
| 6,551,841 B1 | 4/2003 | Wilding et al. |
| 6,576,459 B2 | 6/2003 | Miles et al. |
| 6,586,233 B2 | 7/2003 | Benett et al. |
| 6,602,473 B1 | 8/2003 | Northrup et al. |
| 6,605,213 B1 | 8/2003 | Ammann et al. |
| 6,656,724 B1 | 12/2003 | Heimberg et al. |
| 6,657,169 B2 | 12/2003 | Brown et al. |
| 6,660,517 B1 | 12/2003 | Wilding et al. |
| 6,670,153 B2 | 12/2003 | Stern |
| 6,677,151 B2 | 1/2004 | Sandell |
| 6,699,713 B2 | 3/2004 | Benett et al. |
| 6,703,236 B2 | 3/2004 | Atwood et al. |
| 6,756,019 B1 | 6/2004 | Dubrow et al. |
| 6,762,049 B2 | 7/2004 | Zou et al. |
| 6,767,512 B1 | 7/2004 | Lurz et al. |
| 6,814,934 B1 | 11/2004 | Higuchi |
| 6,830,936 B2 | 12/2004 | Anderson et al. |
| 6,875,602 B2 | 4/2005 | Gutierrez |
| 6,962,821 B2 | 11/2005 | Danssaert et al. |
| 7,005,617 B2 | 2/2006 | Brown |
| 7,008,789 B2 | 3/2006 | Gambini et al. |
| 7,030,340 B2 | 4/2006 | Knoche |
| 7,051,536 B1 | 5/2006 | Cohen et al. |
| 7,074,367 B2 | 7/2006 | Lurz et al. |
| 7,133,726 B1 | 11/2006 | Atwood et al. |
| 7,164,077 B2 | 1/2007 | Venkatasubramania |
| 7,183,103 B2 | 2/2007 | Gambini et al. |
| 7,238,321 B2 | 7/2007 | Wittwer et al. |
| 7,311,794 B2 | 12/2007 | Joseph et al. |
| 7,417,726 B2 | 8/2008 | Kao et al. |
| 7,429,479 B2 | 9/2008 | Harding et al. |
| 7,460,223 B2 | 12/2008 | Harding et al. |
| 7,504,241 B2 | 3/2009 | Atwood et al. |
| 7,560,273 B2 | 7/2009 | Sandell |
| 7,611,674 B2 | 11/2009 | Heimberg et al. |
| 7,771,933 B2 | 8/2010 | Arciniegas et al. |
| 7,833,709 B2 * | 11/2010 | Joseph ............... B01L 3/50851 435/288.4 |
| 2001/0055765 A1 | 12/2001 | O'Keefe et al. |

(56) References Cited

U.S. PATENT DOCUMENTS

| | | |
|---|---|---|
| 2002/0030044 A1 | 3/2002 | Brown |
| 2002/0060156 A1 | 5/2002 | Mathies et al. |
| 2002/0068357 A1 | 6/2002 | Mathies et al. |
| 2002/0072112 A1 | 6/2002 | Atwood et al. |
| 2002/0072113 A1 | 6/2002 | Barbera-Guillem et al. |
| 2002/0110899 A1 | 8/2002 | Wheatcroft |
| 2002/0127660 A1 | 9/2002 | Danssaert et al. |
| 2002/0144771 A1 | 10/2002 | Kuczynski |
| 2002/0182544 A1 | 12/2002 | Chan-Park et al. |
| 2003/0006003 A1 | 1/2003 | Matsuoka |
| 2003/0008286 A1 | 1/2003 | Zou et al. |
| 2003/0032191 A1 | 2/2003 | Hilson et al. |
| 2003/0040011 A1 | 2/2003 | Barth et al. |
| 2003/0040104 A1 | 2/2003 | Barbera-Guillem |
| 2003/0138829 A1 | 7/2003 | Unger et al. |
| 2003/0138941 A1* | 7/2003 | Gong .................. B01L 3/5027 435/287.2 |
| 2003/0157509 A1 | 8/2003 | Mirzabekov et al. |
| 2003/0199081 A1 | 10/2003 | Wilding et al. |
| 2003/0214994 A1 | 11/2003 | Schicke et al. |
| 2004/0018610 A1 | 1/2004 | Sandell |
| 2004/0029303 A1 | 2/2004 | Hart et al. |
| 2004/0060917 A1 | 4/2004 | Liu et al. |
| 2004/0072334 A1 | 4/2004 | Benett et al. |
| 2004/0096958 A1 | 5/2004 | Pottathil et al. |
| 2004/0123880 A1 | 7/2004 | Chiles et al. |
| 2004/0185504 A1 | 9/2004 | Pantoliano et al. |
| 2004/0209331 A1 | 10/2004 | Ririe |
| 2004/0258568 A1 | 12/2004 | Lurz et al. |
| 2005/0019792 A1 | 1/2005 | McBride et al. |
| 2005/0112634 A1 | 5/2005 | Woudenberg et al. |
| 2005/0129581 A1 | 6/2005 | McBride et al. |
| 2005/0145273 A1 | 7/2005 | Atwood et al. |
| 2005/0176155 A1 | 8/2005 | Klein et al. |
| 2005/0225751 A1 | 10/2005 | Sandell et al. |
| 2005/0233324 A1 | 10/2005 | Corbett et al. |
| 2006/0027317 A1 | 2/2006 | Joseph et al. |
| 2006/0030035 A1 | 2/2006 | Joseph et al. |
| 2006/0030036 A1 | 2/2006 | Joseph et al. |
| 2006/0030037 A1 | 2/2006 | Joseph et al. |
| 2006/0046304 A1 | 3/2006 | Shigeura et al. |
| 2006/0073491 A1 | 4/2006 | Joseph et al. |
| 2006/0088931 A1 | 4/2006 | Ririe |
| 2006/0166226 A1 | 7/2006 | Kudoh et al. |
| 2006/0205064 A1 | 9/2006 | Tajima |
| 2006/0246493 A1 | 11/2006 | Jensen et al. |
| 2006/0270026 A1 | 11/2006 | Soh et al. |
| 2007/0084279 A1 | 4/2007 | Huang et al. |
| 2007/0290282 A1 | 12/2007 | Beloy et al. |
| 2008/0026483 A1 | 1/2008 | Oldenburg |
| 2008/0176290 A1 | 7/2008 | Joseph et al. |
| 2008/0288179 A1 | 11/2008 | Kao et al. |
| 2008/0299651 A1 | 12/2008 | Atwood et al. |
| 2010/0233698 A1 | 9/2010 | Joseph et al. |

FOREIGN PATENT DOCUMENTS

| | | |
|---|---|---|
| EP | 0739423 | 1/2002 |
| EP | 1022059 | 8/2002 |
| EP | 1157744 B1 | 3/2004 |
| EP | 1013342 B1 | 4/2004 |
| EP | 0881950 B1 | 7/2004 |
| EP | 0871545 | 1/2005 |
| EP | 1510823 A2 | 3/2005 |
| EP | 0733098 B1 | 1/2006 |
| EP | 1539353 B1 | 2/2006 |
| EP | 1510823 A3 | 7/2006 |
| GB | 2370112 | 6/2002 |
| JP | 2002-010777 | 1/2002 |
| JP | 2003-014753 | 1/2003 |
| JP | 2003-107094 | 4/2003 |
| JP | 2006-223309 | 8/2006 |
| WO | WO 97/42500 A1 | 11/1997 |
| WO | WO 0109389 | 2/2001 |
| WO | WO 2005/028109 A2 | 3/2005 |
| WO | WO 2005/028110 A2 | 3/2005 |
| WO | WO 2005/028629 A2 | 3/2005 |
| WO | WO 2005/028109 A3 | 7/2005 |
| WO | WO 2005/028110 A3 | 8/2005 |
| WO | WO 2005/108604 A2 | 11/2005 |
| WO | WO 2005/028629 A3 | 6/2006 |
| WO | WO 2006/102264 A1 | 9/2006 |
| WO | WO 2009/083648 A2 | 7/2009 |
| WO | WO 2009/100933 A1 | 8/2009 |
| WO | WO 2009/083648 A3 | 9/2009 |
| WO | WO 2010/140982 A1 | 12/2010 |

OTHER PUBLICATIONS

Beier, M. et al. "Versatile Derivatisation of Solid Support Media for Covalent Bonding on DNA-microchips," Nucleic Acids Research. May 1, 1999. vol. 27. No. 9, pp. 1970-1977.

Guschin, D. et al. "Manual Manufacturing of Oligonucleotide, DNA, and Protein Microchips," Analytical Biochemistry. Aug. 1, 1997. vol. 250. No. 2, pp. 203-211.

Innis et al. "Optimization of PCRs," In: PCR Protocols (Innis, Gelfand, Sninsky and White, eds.). Academic Press, New York. 1990; pp. 3-12.

Joos, B. et al. "Covalent Attachment of Hybridizable Oligonucleotides to Glass Supports," Analytical Biochemistry, Apr. 5, 1997, vol. 247, No. 1, pp. 96-101.

Lin et al. "Fabrication of polydimethylsiloxane (PDMS) pulsating heat pipe," Applied Thermal Engineering. 2009; 29(2-3), pp. 573-580.

McPherson et al. eds. The series Methods in Enzymology (Academic Press, Inc.): PCR 2: A practical approach. Oxford University Press, New York, 1995, 332 pages.

Quirk et al. Semiconductor Manufacturing Technology, Prentice Hall, NJ, 2001, 55 pages.

Rychlik et al. "Optimization of the annealing temperature for DNA amplification in vitro," Nucleic Acids Research 1990; 18 (21):6409-6412.

Sambrook et al. Molecular Cloning: A Laboratory Manual, 2nd Edition, 1989, 1546 pages.

Wolf, S. Silicon Processing for the VLSI ERA, vol. 1-4, Lattice Press, 2002, 822 pages.

Yoon et al. "Precise temperature control and rapid thermal cycling in a micromachined DNA polymerase Xchain reaction chip," J. Micromech. Microeng. 2002; 1X2:813-823.

International Search Report dated Nov. 18, 2005 for PCT Application No. US2005/018297.

International Search Report dated Jun. 11, 2008 for PCT Application No. US 2008/000860.

* cited by examiner

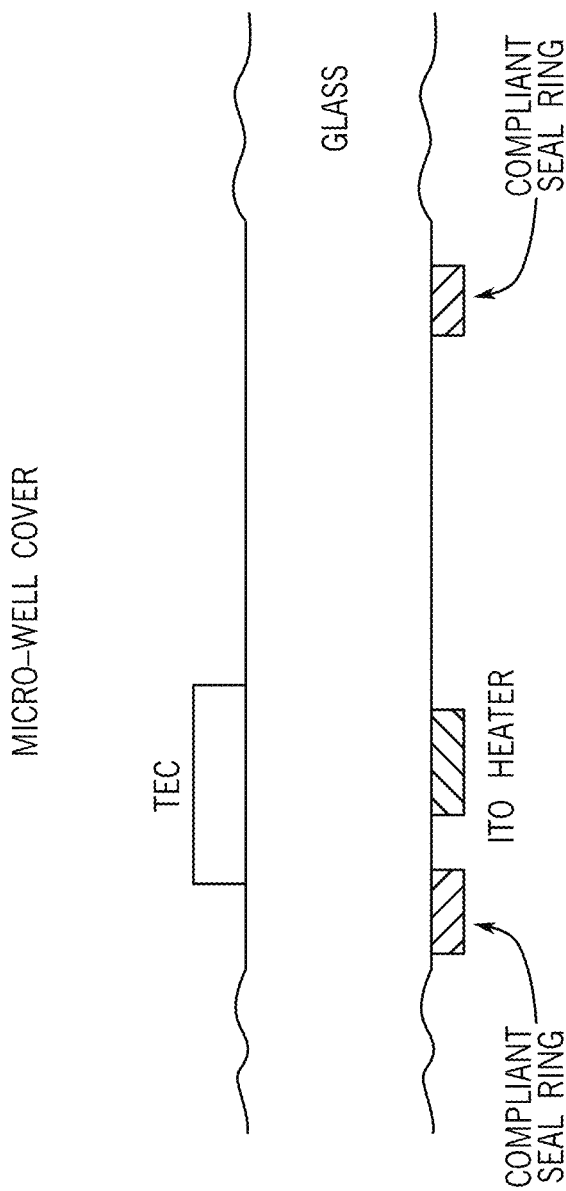

PCR product of a 122 bp fragment of the G6PDH gene in the presence of 20000 × diluted SYBR Green I (100 nl sample)

THERMO-CONTROLLABLE HIGH-DENSITY CHIPS FOR MULTIPLEX ANALYSES

CROSS-REFERENCE TO RELATED APPLICATIONS

This application claims the priority benefit of U.S. Provisional Application Ser. No. 60/630,789 filed Nov. 24, 2004, and U.S. patent application Ser. No. 10/857,552 filed May 28, 2004, all of which are hereby incorporated herein by reference in their entirety.

TECHNICAL FIELD

This invention relates to miniaturized instruments for conducting chemical reactions where control of the reaction temperature is desired or required. Specifically, the invention relates to chips and optical systems for performing temperature-dependent chemical reactions. The apparatus and methods embodied in the present invention are particularly useful for high-throughput and low-cost amplification of nucleic acids.

BACKGROUND OF THE INVENTION

The advent of Polymerase Chain Reaction (PCR) since 1983 has revolutionized molecular biology through vastly extending the capability to identify, manipulate, and reproduce DNA. Nowadays PCR is routinely practiced in the course of conducting scientific researches, clinical diagnostics, forensic identifications, and environmental studies. PCR has been automated through the use of thermal stable DNA polymerases and a machine commonly known as "thermal cycler".

Performing a large quantity of PCR with the conventional thermal cycler has been rather expensive. This is partly due to the intrinsic limitations of the conventional instrument. The conventional thermal cycler employs metal heating blocks and cooling reservoirs to carry out the thermal cycling of reaction samples in plastic microfuge tubes. Because the instrument has a large thermal mass and the plastic tubes have low heat conductivity, high level of electrical power is required to operate the instrument.

In recent years, the advancement in microfabrication technology enabled the production of miniaturized devices integrated with electrical, optical, chemical or mechanical elements. The technology embodies a range of fabrication techniques including low-pressure vapor deposition, photolithography, and etching. Based on these techniques, miniaturized devices containing silicon channels coupled to micro-heaters have been proposed (see, e.g., U.S. Pat. Nos. 5,639,423, 5,589,136 and 5,587,128). While the channel- or chamber-based design in principle reduces the thermal mass and the reaction volume, it still suffers from other practical drawbacks. In particular, the channels or chambers by design are not amenable to automated sealing that prevents evaporation and/or cross contamination of the reaction samples.

There thus remains a considerable need for small, mass produced, and disposable devices designed to perform high-throughput amplification of nucleic acids. A desirable device would allow (a) multiplexing an enormous quantity of amplification reactions; (b) automated and targeted sealing of the reaction sites on the devices; and (c) monitoring the progress of the amplification reaction in real time. The present invention satisfies these needs and provides related advantages as well.

SUMMARY OF THE INVENTION

A principal aspect of the present invention is the design of miniaturized devices applicable for multiplex analyses of individual molecules, and/or simultaneous performance of a vast number of chemical reactions. The devices and methods of the present invention simplify the laborious and expensive procedures of performing chemical reactions where a control of the reaction temperature is desired or required.

Accordingly, in one embodiment, the present invention provides a chip for varying and/or maintaining temperature of a reaction sample. The chip comprises an array of thermo-controllable units that is in thermal contact with a heating element, wherein the varying and/or maintaining of temperature is achieved by controlling the heating element alone, and wherein individual unit within the array comprises a micro well for receiving and confining the reaction sample.

In another embodiment, the present invention provides a chip for varying and/or maintaining a reaction sample that comprises an array of thermo-controllable units, wherein the chip has a surface density of at least about one thermo-controllable unit per 1 $mm^2$, and wherein a unit within the array comprises a micro well for receiving and confining the reaction sample, and a heating element in thermal contact with the micro well.

In yet another embodiment, the present invention provides a chip that comprises two arrays of thermo-controllable units, wherein one array is arranged in one orientation along the upper surface, and wherein the other array is arranged in an opposite orientation along the bottom surface.

In a further embodiment, the present invention provides a chip comprising an indium tin oxide heater (ITO-heater) in a glass plate that is coupled to an array of thermo-controllable units fabricated in the chip.

In one aspect of these embodiments, the micro well is sealed upon filling the reaction sample. Preferably, the well is sealed by (a) applying a radiation-curable adhesive along peripheral dimensions defining an open surface of the micro well; (b) placing a cover to encompass the peripheral dimensions that define the open surface of the micro well; and (c) exposing the micro well to a radiation beam to effect the sealing. A wide range of radiation curable adhesive is applicable for the present invention. They include but are not limited to a diversity of acrylics, acrylates, polyurethanes (PUR), polyesters, vinyl, vinyl esters, and epoxies that are curable by radiation beams such as UV radiation and other radiation beams of various frequencies.

In certain aspects, the micro well in the subject chips are about 10 mm to about 100 µm in length, about 10 mm to about 100 µm in width, and about 10 mm to about 100 µm in depth. The volume of the micro well is generally small, ranging from about 0.001 µl to about 100 µl. Where desired, not all of the thermo-controllable units within an array are filled with reaction sample. Preferably, any two thermo-controllable units filled with a reaction sample are separated by at least one unfilled thermo-controllable unit. In certain aspects, the subject chips have a surface density of at least one thermo-controllable unit per $cm^2$, preferably at least about 10 per $cm^2$, or preferably at least about 100 per $cm^2$, or preferably in the range of about 5 thermo-controllable units to about 50 thermo-controllable units per $mm^2$. Where desired, the chips are operatively linked to a dispensing system for placing a reaction sample into the thermo-controllable units.

In other aspects, the thermo-controllable units of the subject chips can be arranged in different temperature zones, each of which can be separately controlled. In general, the micro well within each unit is in thermal contact with a heating element that can be made of metal or semi-conducting material. Preferred heating element is an indium-tin-oxide (ITO) heater. Heating element can be located within the micro well, or can be attached to the upper or bottom, or both surfaces of the micro well. To prevent evaporation and condensation of the reaction sample on the upper surface of the well, the upper surface can be maintained at a higher temperature than the bottom surface. In preferred embodiments, a plurality of grooves is fabricated to the bottom surface of the chip. The presence of the grooves greatly facilitates passive heat dissipation during thermal cycling. In other embodiments, the subject chips have a ramp temperature time about 10° C. or higher per second, preferably about 25° C. or higher per second. In other preferred embodiments, the subject chips may comprise temperature sensors in thermal contact with the micro wells.

In certain embodiments, the subject chips are operatively coupled to an optical system that detects optical signals emitted from the reaction sample. In preferred embodiments, the subject chips are fabricated with photon-sensing elements in optical communication with the micro wells where chemical reactions are taking place. Representative photon-sensing elements include photo multiplier tube, charge coupled device, avalanche photo diode, gate sensitive FET's and nano-tube FET's, and P-I-N diode.

The present invention also provides an apparatus for conducting a chemical reaction requiring cycling at least two temperature levels. The apparatus comprises a chip of the present invention and an optical system that is operatively coupled to the chip. In this apparatus, the optical system detects an optical signal such as luminescent signal coming from the micro well fabricated in the chip. In one aspect, the optical system monitors the optical signal over a multiple-cycle period. In another aspect, the optical system detects an optical signal that is proportional to the amount of product of the chemical reaction taking place in the micro well over a multiple-cycle period. The optical system can include a spectrum analyzer that is composed of an optical transmission element and a photon-sensing element. Preferred optical transmission element can be selected from the group consisting of multi-mode fibers (MMF), single-mode fibers (SMF) and a waveguide. Preferred photon-sensing element can be selected from the group consisting of photo multiplier tube, charge coupled device, avalanche photo diode, gate sensitive FET's and nano-tube FET's, and P-I-N diode.

In a preferred embodiment, the present invention provides an apparatus for multiplexed analysis. The apparatus comprises an array of micro wells for containing and confining reaction samples, wherein the array is optically linked to (a) an optical multiplexer adapted for receiving and multiplexing a plurality of incoming beams of one or more different wavelengths; (b) an optical switch adapted for redirecting the multiplexed wavelengths of (a) to individual output fibers, wherein each of the individual output fibers optically linked to a micro well of the array, said micro well being coupled to a spectrum analyzer that spectrally analyzes optical signals coming from the micro well.

The apparatus of the present invention is capable of performing a vast diversity of chemical reactions. The subject apparatus is particularly suited for performing enzymatic reactions, including but not limited to nucleic acid amplification reaction that encompasses PCR, quantitative polymerase chain reaction (qPCR), nucleic acid sequencing, ligase chain polymerase chain reaction (LCR-PCR), reverse transcription PCR reaction (RT-PCR), reverse transcription, and nucleic acid ligation.

Also provided by the present invention is a method of varying and/or maintaining a temperature of a reaction sample. The method involves (a) placing the reaction sample into a micro well fabricated in a chip, said micro well being in thermal contact with a heating element, wherein the varying and/or maintaining of temperature is achieved by controlling the heating element alone, and wherein the micro well receives and confines the reaction sample, and is sealed when filled with the reaction sample; (b) applying a voltage to the heating element thereby varying and/or maintaining the temperature of the reaction sample. The step of applying a voltage can be effected by processing a predetermined algorithm stored on a computer readable media operatively linked to the heating element. The Method may also involve cycling the applying step to raise and lower the temperature of the reaction sample.

Further provided is a method of using a chip of the present invention to conduct a chemical reaction that involves a plurality of reaction samples and requires cycling at least two temperature levels. The method comprises: (a) providing a subject chip; (b) placing the plurality of reaction samples into the thermo-controllable units; and (c) controlling the heating element to effect cycling at least two temperature levels. In one aspect of this embodiment, the controlling step comprises processing sensor signals retrieved from a temperature sensor operatively linked to a thermo-controllable unit based on protocol stored on a computer readable medium. In another aspect, the method employs a subject chip operatively coupled to an optical system that detects optical signals emitted from the reaction sample. In a preferred aspect, the optical system detects the optical signal without the need for opening the micro well once the chemical reaction is initiated. In yet another preferred aspect, the optical signals detected are proportional to the amount of product of the chemical reaction. A variety of chemical reactions including a specific protein-protein interaction and enzymatic reactions can be performed using this method.

The present invention also provides a method of using the subject apparatus comprising the chip and optical system described herein to detect the presence or absence of a target nucleic acid in a plurality of reaction samples. In this method, the formation of amplified target nucleic acids indicates the presence of the target nucleic acid in the reaction sample. In certain aspects, the amplified target nucleic acids are observed by transmitting excitation beams into the wells containing the reaction samples, and detecting the optical signals coming from the micro well. In other aspects, formation of amplified target nucleic acids is observed by transmitting excitation beams into the wells containing the reaction samples at a plurality of times during the amplification, and monitoring the optical signals coming from the micro well at each of the plurality of times.

BRIEF DESCRIPTION OF THE DRAWINGS

FIG. 6B depicts an exemplary cover placed on top of the exemplary chip shown in 6A.

DETAILED DESCRIPTION OF THE INVENTION

Figure 1:
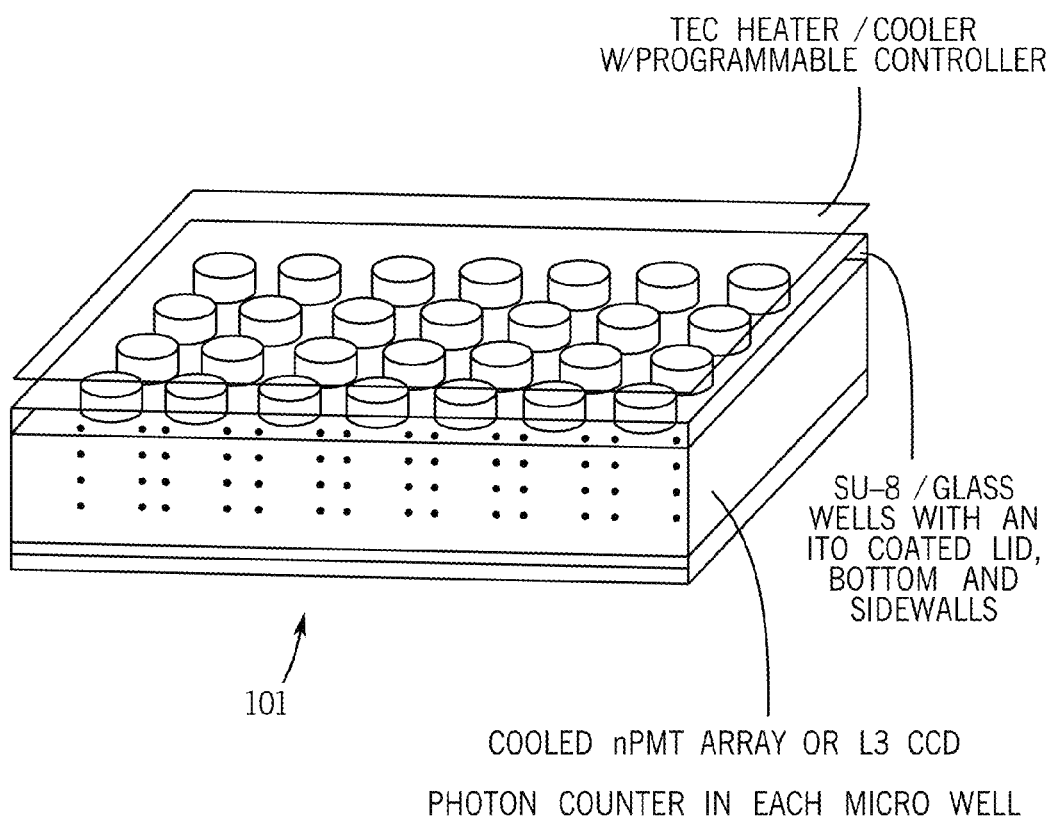
FIG. 1 depicts one illustrative chip design 101 having an integrated heating element and photon-sensing element.

General Techniques:

The practice of the present invention will employ, unless otherwise indicated, conventional techniques of Integrated Circuit (IC) processing biochemistry, chemistry, molecular biology, genomics and recombinant DNA, which are within the skill of the art. See, e.g., Stanley Wolf et al., SILICON PROCESSING FOR THE VLSI ERA, Vols 1-4 (Lattice Press); Michael Quirk et al., SEMICONDUCTOR MANUFACTURING TECHNOLOGY; Sambrook, Fritsch and Maniatis, MOLECULAR CLONING: A LABORATORY MANUAL, $2^{nd}$ edition (1989); the series METHODS IN ENZYMOLOGY (Academic Press, Inc.): PCR 2: A PRACTICAL APPROACH (M. J. MacPherson, B. D. Hames and G. R. Taylor eds. (1995).

Definitions

As used in the specification and claims, the singular form "a", "an" and "the" include plural references unless the context clearly dictates otherwise.

"Luminescence" is the term commonly used to refer to the emission of light from a substance for any reason other than a rise in its temperature. In general, atoms or molecules emit photons of electromagnetic energy (e.g., light) when then move from an "excited state" to a lower energy state (usually the ground state); this process is often referred to as "radioactive decay". There are many causes of excitation. If exciting cause is a photon, the luminescence process is referred to as "photoluminescence". If the exciting cause is an electron, the luminescence process is referred to as "electroluminescence". More specifically, electroluminescence results from the direct injection and removal of electrons to form an electron-hole pair, and subsequent recombination of the electron-hole pair to emit a photon. Luminescence which results from a chemical reaction is usually referred to as "chemiluminescence". Luminescence produced by a living organism is usually referred to as "bioluminescence". If photoluminescence is the result of a spin-allowed transition (e.g., a single-singlet transition, triplet-triplet transition), the photoluminescence process is usually referred to as "fluorescence". Typically, fluorescence emissions do not persist after the exciting cause is removed as a result of short-lived excited states which may rapidly relax through such spin-allowed transitions. If photoluminescence is the result of a spin-forbidden transition (e.g., a triplet-singlet transition), the photoluminescence process is usually referred to as "phosphorescence". Typically, phosphorescence emissions persist long after the exciting cause is removed as a result of long-lived excited states which may relax only through such spin-forbidden transitions. A "luminescent label" or "luminescent signal" may have any one of the above-described properties.

A "primer" is a short polynucleotide, generally with a free 3' —OH group, that binds to a target nucleic acid (or template) potentially present in a sample of interest by hybridizing with the target nucleic acid, and thereafter promoting polymerization of a polynucleotide complementary to the target.

The terms "operatively linked to" or "operatively coupled to" are used interchangeably herein. They refer to a juxtaposition wherein the components so described are in a relationship permitting them to function in their intended manner.

Structure of the Chips of the Present Invention

A central aspect of the present invention is the design of miniaturized devices applicable for multiplexed analyses of individual molecules, and/or simultaneous performance of a vast number of chemical reactions. Distinguished from the previously reported micro-capillary devices or other channel-based instruments, the present invention provides a highly automated, miniaturized, analytical instrument that allows manipulations with precise control of temperature, evaporation, small-volume reagent delivery, product detection in a multiplexed fashion.

In one embodiment, the present invention provides chips for varying and/or maintaining temperature of a reaction sample. The chips embodied in the present invention generally comprise at least one array of thermo-controllable units. The individual units within the array are separated from each other by a physical barrier resistant to the passage of liquids. These units generally form indented areas referred to as "micro wells". A micro well can be open at the top, but it must be enclosed otherwise and physically isolated from other wells to restrict passage of liquids. Accordingly, the micro well has at least one cavity suitable for receiving and confining reaction sample. By "confining reaction sample" it is meant that the mobility of the reaction sample is restricted by a physical barrier, and the sample is prevented from flowing into another site once it is applied to the micro well of a thermo-controllable unit.

The micro well may be fabricated in any convenient size, shape or volume. The well may be about 10 mm to about 100 µm in length, about 10 mm to 100 µm in width, and about 10 mm to 100 µm in depth. In general, the well has a transverse sectional area in the range of about 0.01 mm$^2$ to about 100 mm$^2$. The transverse sectional area may be circular, elliptical, oval, conical, rectangular, triangular, polyhedral, or in any other shape. The transverse area at any given depth of the well may also vary in size and shape.

The overall size of the chip ranges from a few microns to a few centimeters in thickness, and from a few millimeters to 50 centimeters in width or length. Preferred chips have an overall size of about 500 micron in thickness and may have any width or length depending on the number of micro wells desired.

The cavity of each well may take a variety of configurations. For instance, the cavity within a micro well may be divided by linear or curved walls to form separate but adjacent compartments, or by circular walls to form inner and outer annular compartments.

The micro well typically has a volume of less than 500 µl, preferably less than 50 ul. The volume may be less than 10 ul, or even less than 1 ul. Where desired, the micro well can be fabricated in which the inner surface area to volume ratio is greater than about 1 mm$^2$/1 ul, or greater than 5 mm$^2$/1 ul, or even greater than 10 mm$^2$/1 ul. Increasing the surface area to volume ratio facilitates heat transfer through the thermal-controllable unit, thereby reducing the ramp time of a thermal cycle.

A micro well of high inner surface to volume ratio may be coated with materials to reduce the possibility that the reactants contained therein may interact with the inner surfaces of the well. Coating is particularly useful if the reagents are prone to interact or adhere to the inner surfaces undesirably. Depending on the properties of the reactants, hydrophobic or hydrophilic coatings may be selected. A variety of appropriate coating materials are available in the art. Some of the materials may covalently adhere to the surface, others may attach to the surface via non-covalent interactions. Non-limiting examples of coating materials include silanization reagent such as dimethychlorosilane, dimethydichlorosilane, hexamethyldisilazane or trimethylchlorosilane, polymaleimide, and siliconizing reagents such as silicon oxide, Aquasil™, and Surfasil™. Additional suitable coating materials are blocking agents such as amino acids, or polymers including but not limited to polyvinylpyrrolidone, polyadenylic acid and polymaleimide.

The surface of the micro well can further be altered to create adsorption sites for reaction reagents. These sites may comprise linker moieties for attachment of biological or chemical compound such as a simple or complex organic or inorganic molecule, a peptide, a protein (e.g. antibody) or a polynucleotide.

The total number of thermo-controllable units fabricated on the chip will vary depending on the particular application in which the subject chips are to be employed. To accommodate the need for simultaneous performance of a vast number of reactions, the subject chips will generally comprise at least about 100 thermo-controllable units, usually at least about 500 thermo-controllable units, and more usually at least about 1000 units. The density of the thermo-controllable units on the chip surface may vary depending on the particular application. High-density chips usually contains on the surface at least about 10 thermo-controllable units per cm$^2$, or preferably at least about 100 thermo-controllable units per cm$^2$, or preferably in the range of about 5 thermo-controllable units to about 50 thermo-controllable units per mm$^2$.

Figure 2:
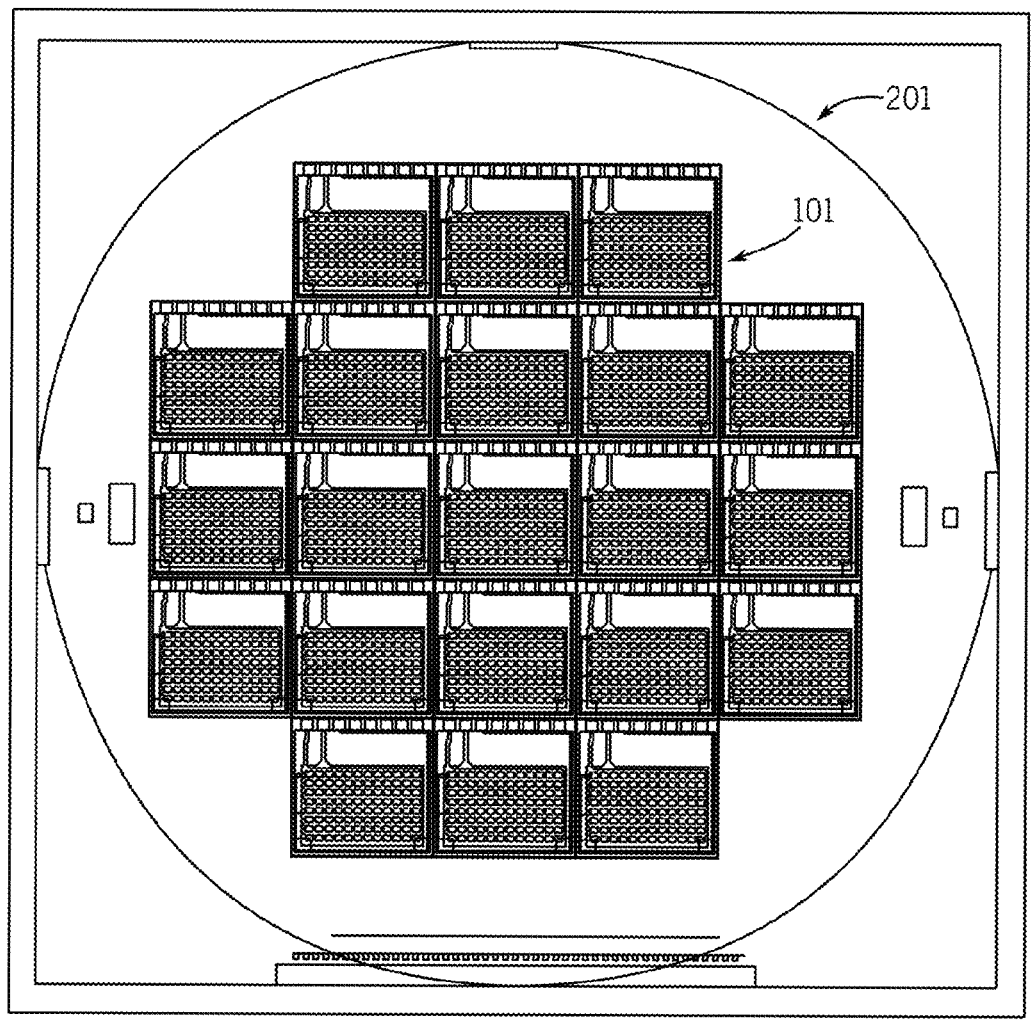
FIG. 2 is a top view of one exemplary chip layout 101 on a circular substrate 201.
Figure 3:
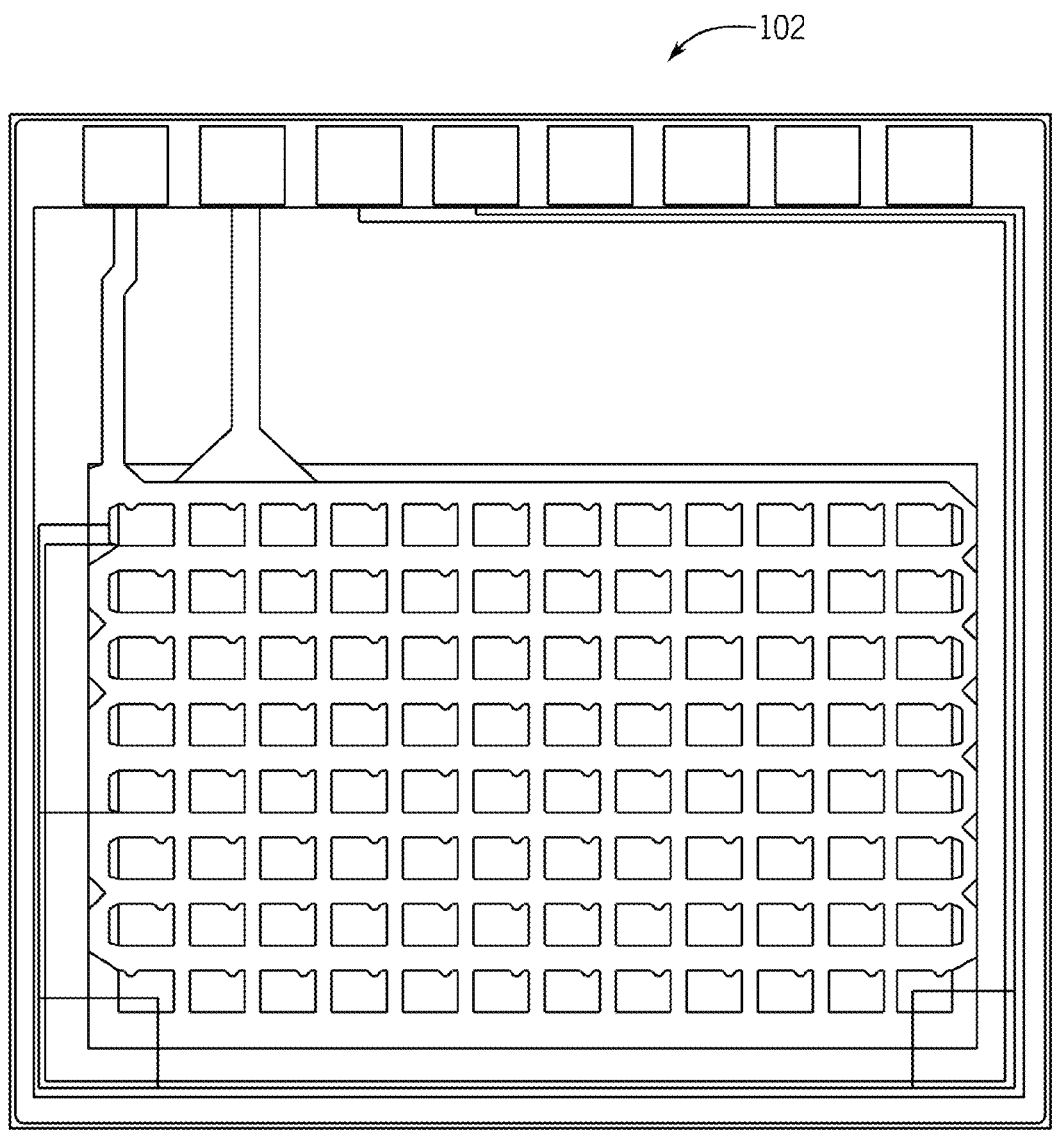
FIG. 3 is a schematic representation of one micro well on the chip.
Figure 4:
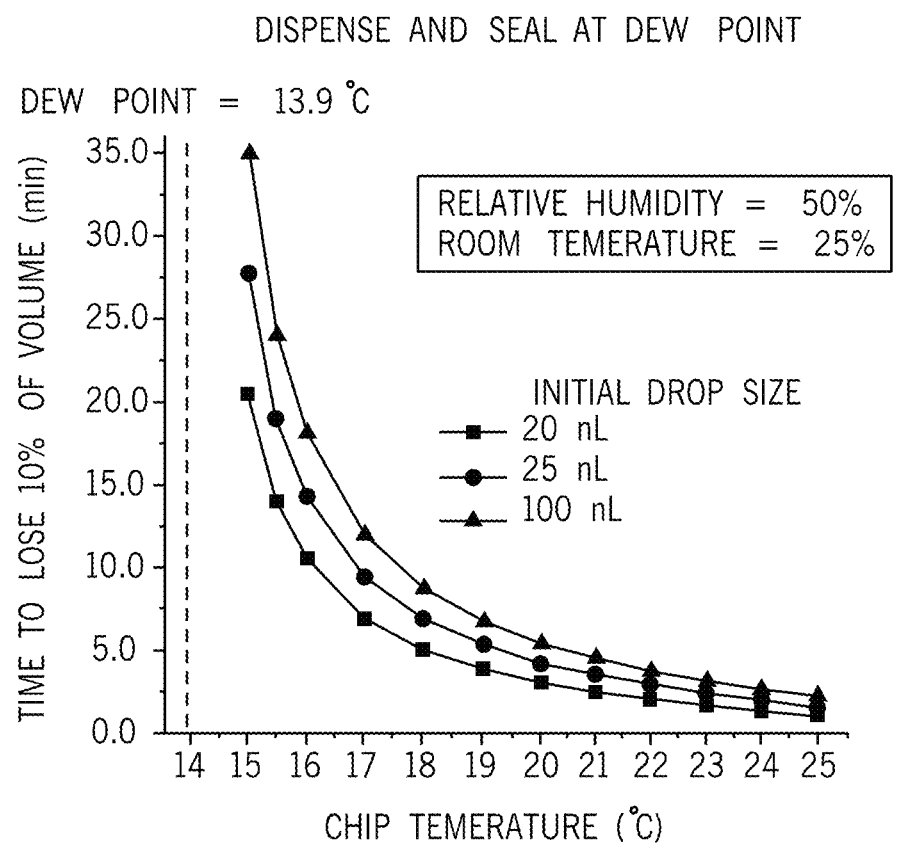
FIG. 4 is a graph plotting the amount of time required to lose 10% reaction sample volume (y-axis) at various temperatures (x-axis). Three different initial droplet volumes, namely 20 nl, 50 nl, and 100 nl are shown. The dew point under the test condition is about 14° C.

The thermo-controllable units of the subject chips can be arrayed in any format across or over the surface of the chip, such as in rows and columns so as to form a grid, in a circular pattern, and the like, see, e.g., FIG. 2. In a preferred embodiment, the thermo-controllable units are arrayed in a format compatible to instrumentation already exists for dispensing reagents and/or reading assays on microtiter plates. That way extensive re-engineering of commercially available fluid handling devices is not required. Accordingly, the thermo-controllable units of the subject chips are preferably arranged in an 8×12 format. Using this format, each chip may have at least 96 thermo-controllable units, preferably at least 384 thermo-controllable units, more preferably at least 1,536 units, and even more preferably 6,144 or 24,576 units. While the number of thermo-controllable units of the 8×12 format chip may be as many as 24,576 or more, it usually does not exceed about 393,216 units, and more usually does not exceed about 6,291,456 units.

Figure 8:
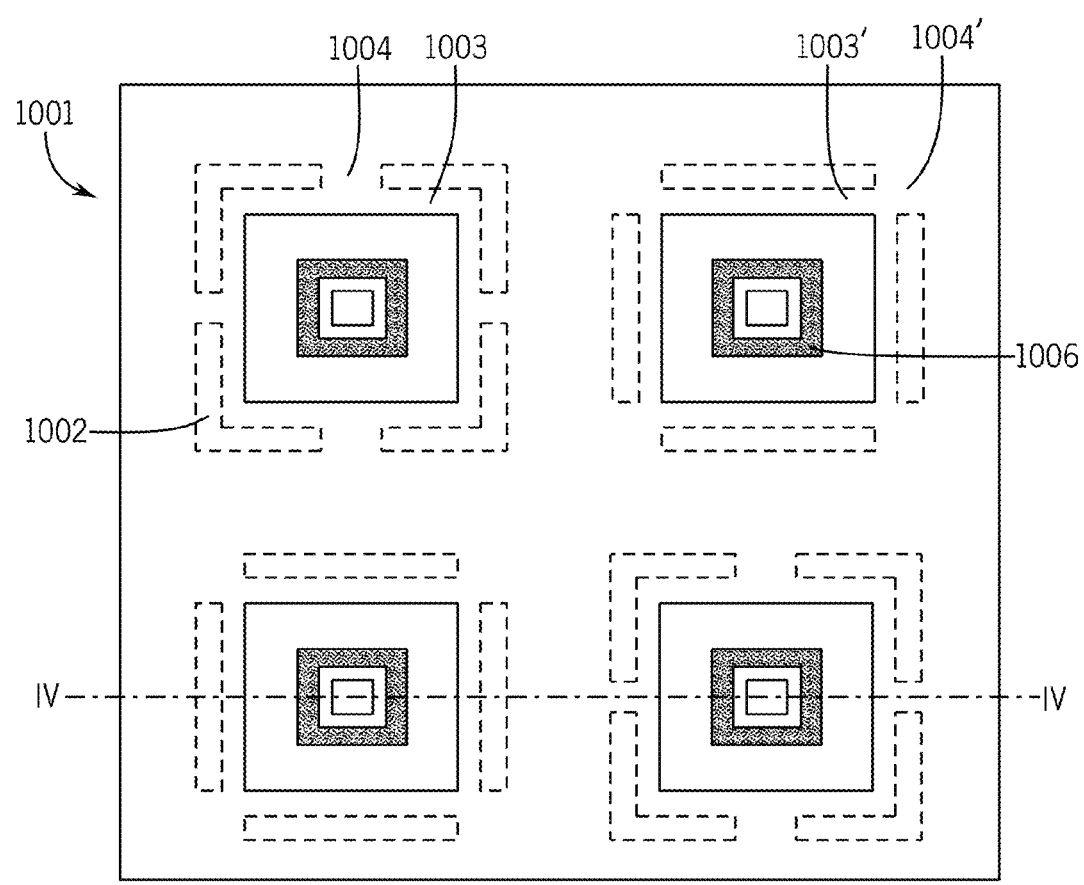
FIG. 8 is a top view of one exemplary chip design 1001. Shown in the figure are 4 thermo-controllable units, each being surrounded at the base by four L-shaped grooves 1002 (dashed lines). Each unit contains an integrated heating element 1006.
Figure 9:
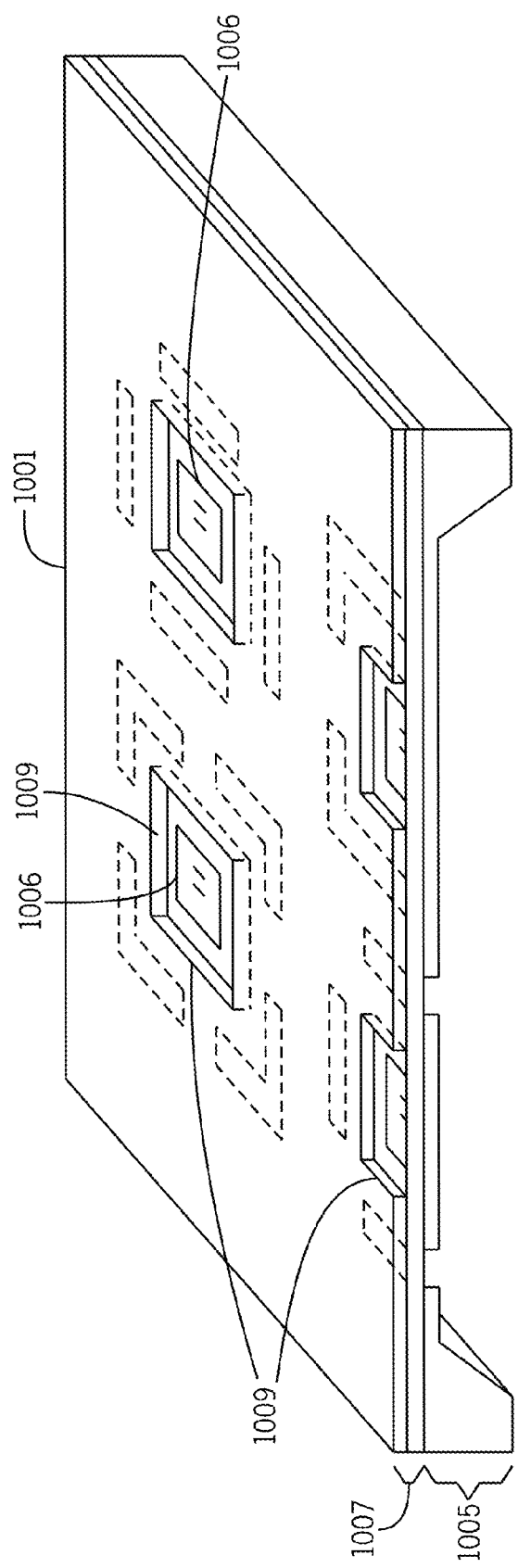
FIG. 9 depicts a side view of the chip design of FIG. 8.
Figure 10:
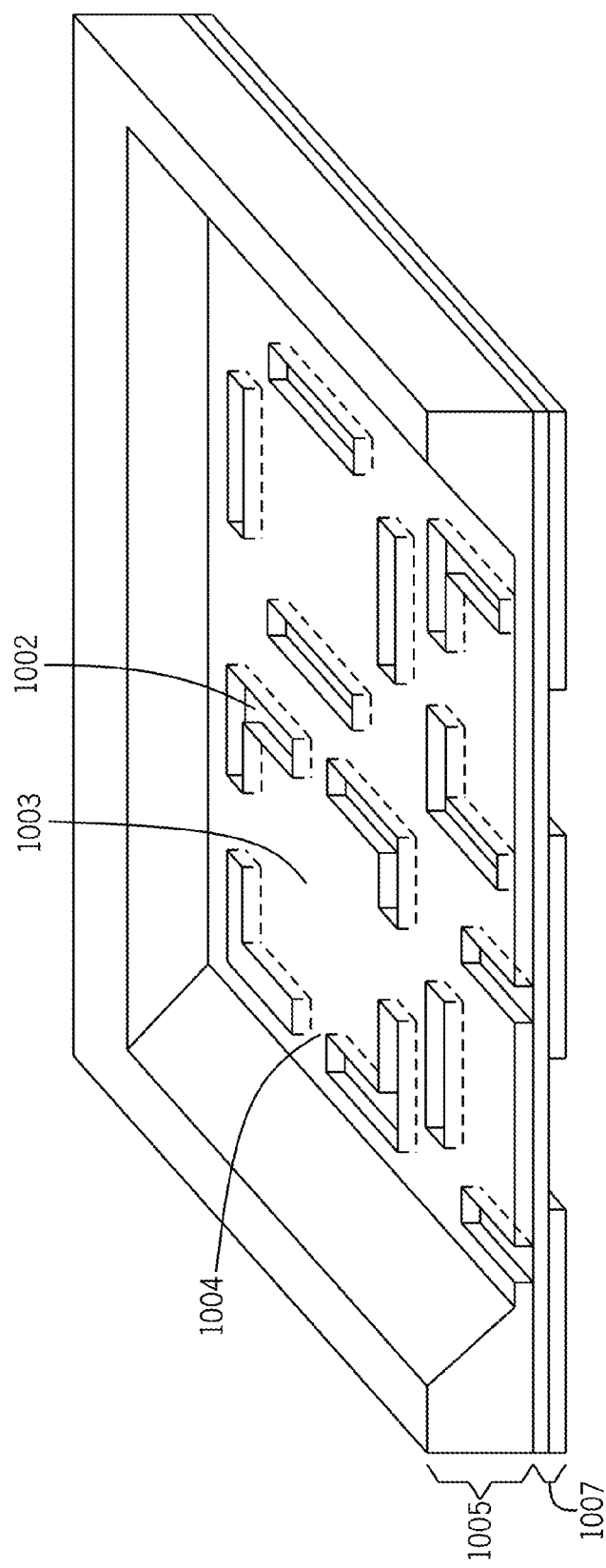
FIG. 10 is a bottom view of the chip design shown in FIG. 8.

The subject chips typically contain one or more grooves etched in at the bottom side of the chip. In general, the grooves are under-trenches, open channels or paths to allow air passage. The grooves reduce the thermal mass of the chip, increase the surface area, and thus enhance the thermal performance of the chips. The grooves can be fabricated in any shapes, including but not limited to circular, elliptical, oval, conical, rectangular, triangular, and polyhedral. The grooves may be further divided by linear or curved walls to form separate but adjacent channels, or by circular walls to form inner and outer annular channels. The dimensions of the grooves will depend on the overall sizes and depths of the chips. The depths of the grooves may range from about one tenth to about nine tenths of the chip depths. The other dimensions, namely widths and lengths, may be shorter, longer or comparable to the corresponding dimensions of the chips. FIGS. 8-10 depict an exemplary groove 1002 design. In particular, the L-shaped grooves surround the base of a thermo-controllable unit. As the air flows through the passageways formed by any of the grooves, it removes heat from the surfaces of thermo-controllable unit by passive heat dissipation, thus increasing the speed of thermal cycling.

The subject chips may contain more than one array of thermo-controllable units. The arrays of thermo-controllable units may align horizontally, longitudinally, or diagonally long the x-axes or the y-axes of the chips. In addition, the arrays may align along curved walls within the chips that divide the arrays to form separate but adjacent compartments.

Figure 13:
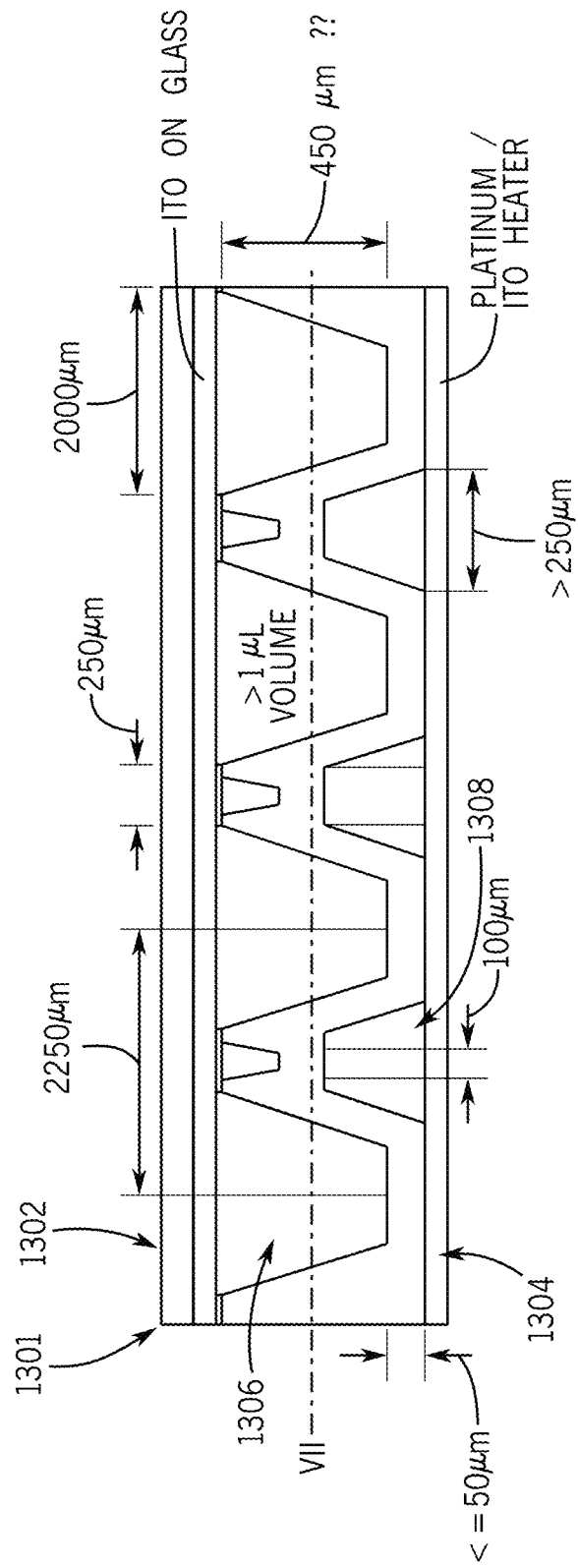
FIG. 13 depicts another illustrative chip design of the present invention. The chip comprises two opposing arrays of thermo-controllable units. Both arrays can be in thermal contact with a heater, one being placed on the upper surface, and another being placed at the bottom surface of the chip.
Figure 14:
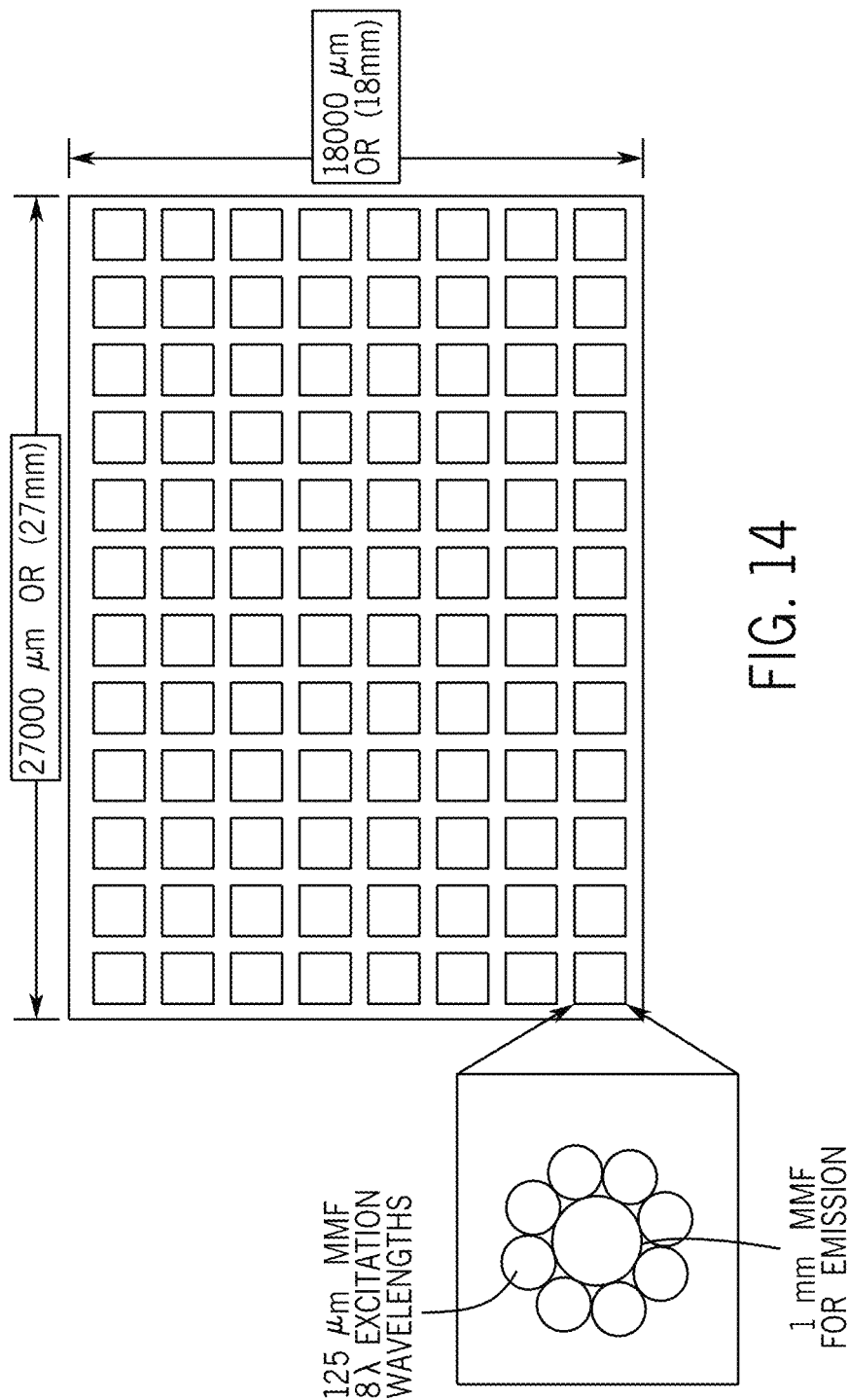
FIG. 14 is a top view of an exemplary chip design adopting a 96-well format. Each well is optically linked to an optical transmission element, multi-mode fibers (MMF).
Figure 15:
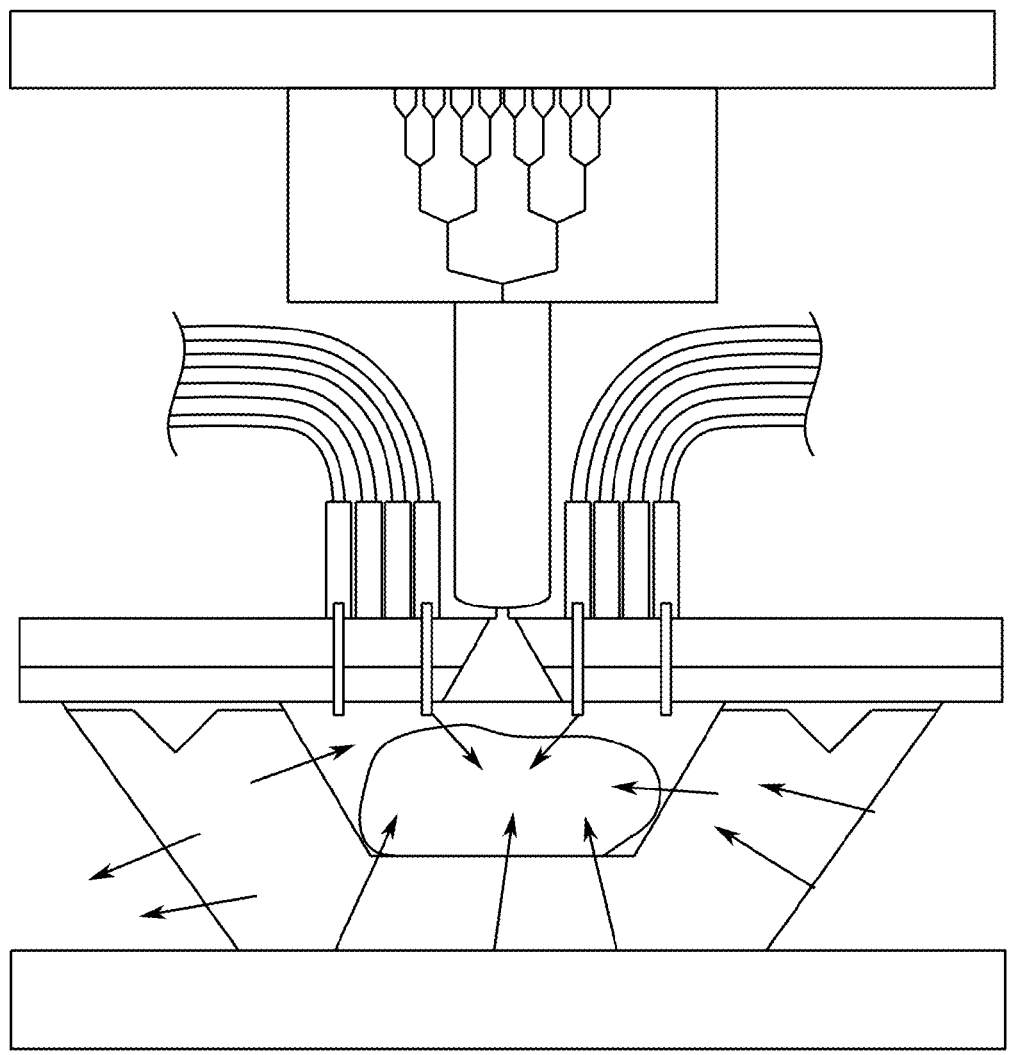
FIG. 15 depicts a side view of the chip shown in FIG. 14. The side view shows a micro well optically linked to an optical system, having an optical transmission element (e.g., multi-mode fibers (MMF)) and photon-sensing element (e.g., CCD) on the top.

A preferred chip of the present invention comprises at least two separate arrays of thermo-controllable units. For instance, one array may be arranged in one orientation along the upper surface of the chip, and the another array may be arranged in an opposite orientation along the bottom surface of the chip. By "opposite orientation" it is meant that one of the arrays is arranged in an inverted manner so that the top surface of each thermo-controllable unit of the array (where the reagents can be added prior to sealing the surface) points away from that of the thermo-controllable units in the opposing array. The two opposing arrays may be arranged such that the base of each thermo-controllable unit is directly opposite to that of the opposing array. Alternatively, the opposing arrays may be staggered such that the thermo-controllable units of the opposing arrays are located in between those thermo-controllable units in the opposing array. FIG. 13 depicts an illustrative chip comprising at least two opposing arrays. In this Figure, the chip 1301 has an upper 1302 and bottom surface 1304. One of the arrays is arranged along the upper surface 1306, and the other is arranged in an opposite orientation along the bottom surface 1308. The thermo-controllable units of the bottom array are positioned in an inverted manner so that the open surface of each unit points away from that of the opposing unit in the chip. The two arrays are staggered so that a cross-section line VII cuts through the thermo-controllable units from both the upper and the bottom arrays.

Though not specifically depicted in FIG. 13, any thermo-controllable units in the upper and/or the bottom arrays may be sealed or unsealed. In addition, any thermo-controllable units within the upper and/or the bottom arrays may be filled or unfilled, with or without the reaction sample. Leaving one or more thermo-controllable units unfilled enhances heat insulation because air is a poor conductor of heat. Accordingly, it is preferable to leave the adjacent thermo-controllable units empty so as to reduce heat transfer from one thermo-controllable unit to the next unit. It is also preferable to leave the entire upper or the bottom array of thermo-controllable units empty in order to minimize heat transfer from one layer to the next.

The subject array of thermo-controllable units is placed in thermal contact with a heating element. This is achieved by integrating the heating element as part of the chip, or by placing the chip in contact with an external heating element.

The heating element can be any heating means, including resistive heater or any other heat-generating device, which converts electrical or electromagnetic energy into heat energy. Preferred heating elements are micro-heaters compatible to the arrayed thermo-controllable units in terms of size and configuration. The micro-heater can be placed as a detachable unit adjacent to, at the base and/or on top of the unit. Alternatively, the micro-heater can be affixed to the interior or the exterior surface of the thermo-controllable unit as an integral part of the unit. The integral heating element may surround the micro well wall, or located at the base of the thermo-controllable unit.

Micro-heaters are typically made of materials having high thermal conductivity and chemical stability. Such materials include but are not limited to metals such as chromium, platinum and gold, and semi-conductors such as ceramic, silicon, and geranium. A material particularly suitable for fabricating the micro-heaters is indium tin oxide (ITO). ITO is a transparent ceramic material with a very high electrical conductivity. Because ITO can be prepared in bulk or in form of thin layer, it is particularly useful as either an integral or an external heating element.

The integral micro-heater generally is made of resistive heating material. Where the heating material is metal, it is generally preferable to coat the surface with an insulating layer to prevent corrosion and/or electrophoresis of the sample components during operation with fluid samples. Coating is usually not necessary in case of non-metal heating material. A variety of protective coatings are available, including those made of, e.g., $SiO_2$, $Si_3N_4$, and teflon. As is apparent to those skilled in the art, certain heating materials can be deposited directly onto the substrate of the thermo-controllable units, and others may be deposited first onto an adhesion layer such as titanium or glass that in turn attaches to the substrate of the units.

Figure 24:
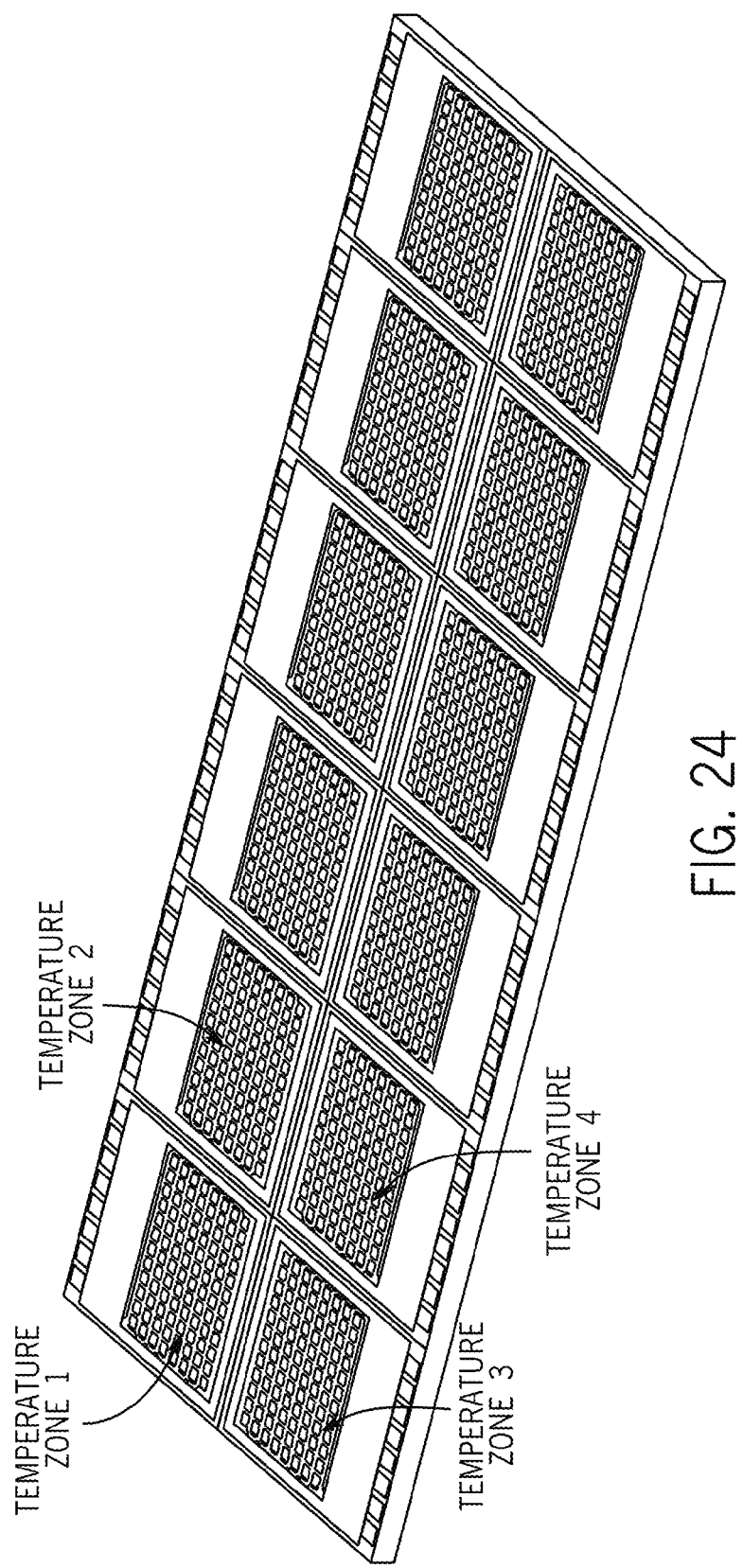
FIG. 24 depicts a chip with more than one temperature zone.

The heating element is typically connected via electric leads to a power source that provides voltage across the element and effects subsequent heating of the thermo-controllable units. The heating element may also be coupled to a temperature sensor that monitors and regulates the temperature of the unit. The temperature sensor may control the temperature and hence the thermal profile of an array of thermo-controllable units. For instance, FIG. 24 depicts an exemplary chip with multiple temperature zones, in which each array of 96 thermo-controllable units represents one temperature zone that is controlled by a temperature sensor and exhibiting a thermal profile distinct from the rest of the temperature zones. Dividing the chip into various temperature zones provides additional flexibility for parallel performance of chemical reactions that require different thermal cycling profiles. Alternatively, the temperature sensor can be coupled to individual thermo-controllable unit so that the temperature of each unit can be independently controlled. The temperature sensor may be included as a detachable unit located adjacent to or at the base of the thermo-controllable unit. It can also be integrated into the interior or the exterior surface of the unit. Furthermore, the temperature sensor can be fabricated as an integral part of the micro-heater.

The subject chips can be provided with an optical system capable of detecting and/or monitoring the results or the progress of chemical reactions taking place in the micro wells of the chips. Such optical system achieves these functions by first optically exciting the reactants, followed by collecting and analyzing the optical signals from the reactants in the micro wells. The optical system applicable for the present invention comprises three elements, namely the optical excitation element, the optical transmission element, and the photon-sensing element. The optical system may also comprise, optionally, an optical selection element.

The optical excitation element act as the source of excitation beams used to optically excite the reactants contained in the micro wells. This element encompasses a wide range of optical sources that generate light beams of different wavelengths, intensities and/or coherent properties. Representative examples of such optical excitation sources include, but are not limited to, lasers, light-emitting diodes (LED), ultra-violet light bulbs, and/or white light sources.

The optical transmission element used in the present invention serves two functions. First, it collects and/or directs the optical excitation sources to the reactants inside the micro wells of the chips. Second, it transmits and/or directs the optical signals emitted from the reactants inside the micro wells of the chips to the photon-sensing element. The optical transmission element suitable for use in the present invention encompasses a variety of optical devices that channel light from one location point to another. Non-limiting examples of such optical transmission devices include optical fibers, optical multiplexers (MUX) and de-multiplexers (DE-MUX), diffraction gratings, arrayed waveguide gratings (AWG), optical switches, mirrors, lenses, collimators, and any other devices that guide the transmission of light through proper refractive indices and geometries.

The photon-sensing element analyzes the spectra of the optical signals coming from the reactants inside the micro wells. Suitable photon-sensing element can detect the intensity of an optical signal at a given wavelength, and preferably can simultaneously measure the intensities of optical signals across a range of wavelengths. Preferably the element may also provide spectrum data analyses to show the spectrum peak wavelength, spectrum peak width, and background spectrum noise measurements. Representative examples of suitable photon-sensing element for the present invention are avalanche photo diodes (APD), charge-coupled devices (CCD), electron-multiplying charge-coupled device (EMCCD), photo-multiplier tubes (PMT), photo-multiplier arrays, gate sensitive FET's, nano-tube FET's, and P-I-N diode. As used herein, CCD includes conventional CCD, electron-multiplying charge-coupled device (EMCCD) and other forms of intensified CCD.

While the subject optical systems can be assembled using many combinations of the various elements, a useful assembly for analyzing the spectra of the excited reactants comprises an optical transmission element and a photon-sensing element. Such assembly is also referred to herein as "spectrum analyzer".

Where desired, the optical system of the present invention can include an optical selection element. This element selects and/or refines the optical properties of the excitation beams before they reaches the reactants contained in the micro wells. The optical selection element can also be employed to select and/or refine the optical signals coming from the reactants in the micro-wells before the signals reach the photon-sensing element. Suitable optical selection element can select and modify a wide range of optical properties, including but not limited to, polarization, optical intensities, wavelengths, phase differences among multiple optical beams, time delay among multiple optical beams. Representative examples of such optical selection elements are polarization filters, optical attenuators, wavelength filters (low-pass, band-pass or high-pass), wave-plates and delay lines.

The aforementioned optical elements can adopt a variety of configurations. They can form integral parts of the subject chips or remain as separate units. All of these elements are commercially available. Accordingly, in one embodiment, the present invention provides a chip in which the optical transmission and photon-sensing elements are fabricated into the chip substrate. In one aspect, the photon-sensing element is integrated into each micro well on the chip that is to be monitored (see, e.g., FIGS. 1, 6A, and 11). In another aspect, more than one type of photon-sensing element is integrated into the micro well to enhance the detection capability or efficiency. In another aspect, the photon-sensing element can be fabricated along the side or at the base of the micro well, or as part of the cover of the micro well. Photon-sensing elements suitable for such configuration include but are not limited to avalanche photo diode, charge coupled devices (including conventional CCD, electron-multiplying charge-coupled device (EMCCD) and other forms of intensified CCD), gate sensitive FET's, nano-tube FET's, P-I-N diode. Avalanche photo diode is particularly preferred because it permits detections of a single photon by amplifying the signal through an avalanche process of electron transfer. These elements together with the supporting circuitry can be fabricated as part of the subject chips using standard IC processing techniques described herein or known in the art.

In another embodiment, the present invention provides an apparatus in which the chip and the optical systems remain as separate units. One aspect of this embodiment encompasses an apparatus for conducting a chemical or biological reaction requiring cycling at least two temperature levels over a multiple-cycle period. The apparatus comprises a chip of the present invention, and an optical system that is operatively coupled to the chip and that detects an optical signal coming from the micro well. Preferably, the optical signals detected are related to the amount of product of the chemical reaction taking place in the micro well.

Figure 16:
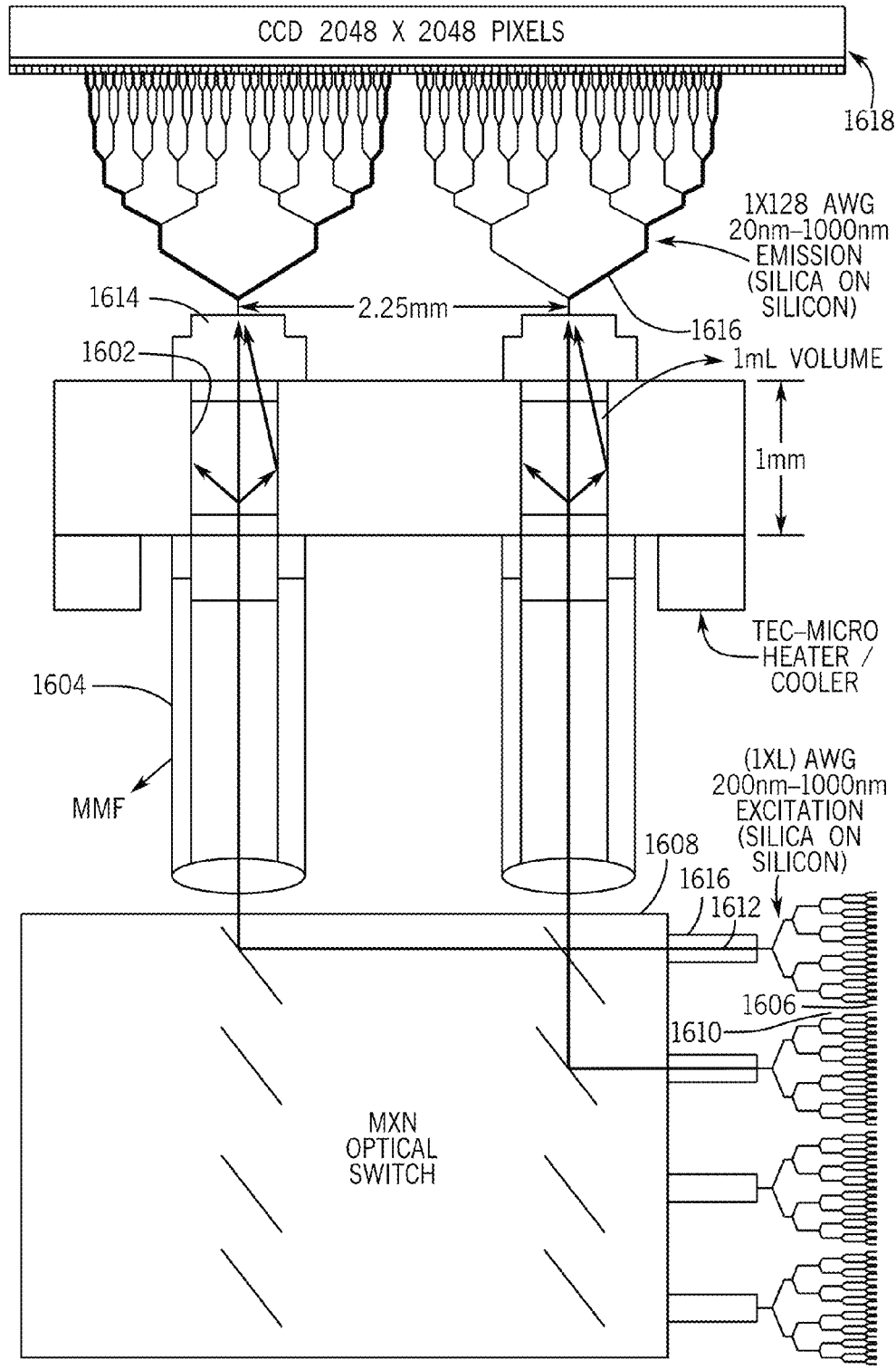
FIG. 16 depicts an apparatus having an array of micro wells optically linked to an optical system.

FIG. 16 illustrates an exemplary optical system of this aspect. This system includes an array of optical transmission element, namely the 1×L (where L is a positive integer) arrayed waveguide 1606, that multiplexes up to L excitation beams 1610 into one optical beam 1612. The excitation beams may have the same or different wavelengths ranging from, e.g., 200 nm to 1000 nm. A plurality of M (where M is a positive integer) arrayed waveguides, each channeling a multiplexed beam, are connected to an M×N optical switch 1608 via the respective optical fiber 1616. The M×N optical switch can direct M input excitation beams from the arrayed waveguide 1606 to any one of its N output ports. Each of the N output ports is operatively coupled to a micro well through an optical fiber 1604. Suitable optical fibers channeling the excitation beams to the micro well may include multi-mode fibers (MMF) and single-mode fibers (SMF). Upon excitation with the incident light beams, optical signals are generated from the reactants inside the micro wells. These optical signals are then collected via an optical collimator 1614 to a 1×P (where P is a positive integer) arrayed waveguide 1616 which de-multiplexes the optical signals. The de-multiplexed optical signals are then transmitted to a spectrum analyzer, here a charge-coupled device (CCD) 1618 (which is part of the spectrum analyzer), for a spectrum analysis. CCDs having high number of pixels are preferred as they provide a higher resolution of the optical signals being examined.

Figure 17A:
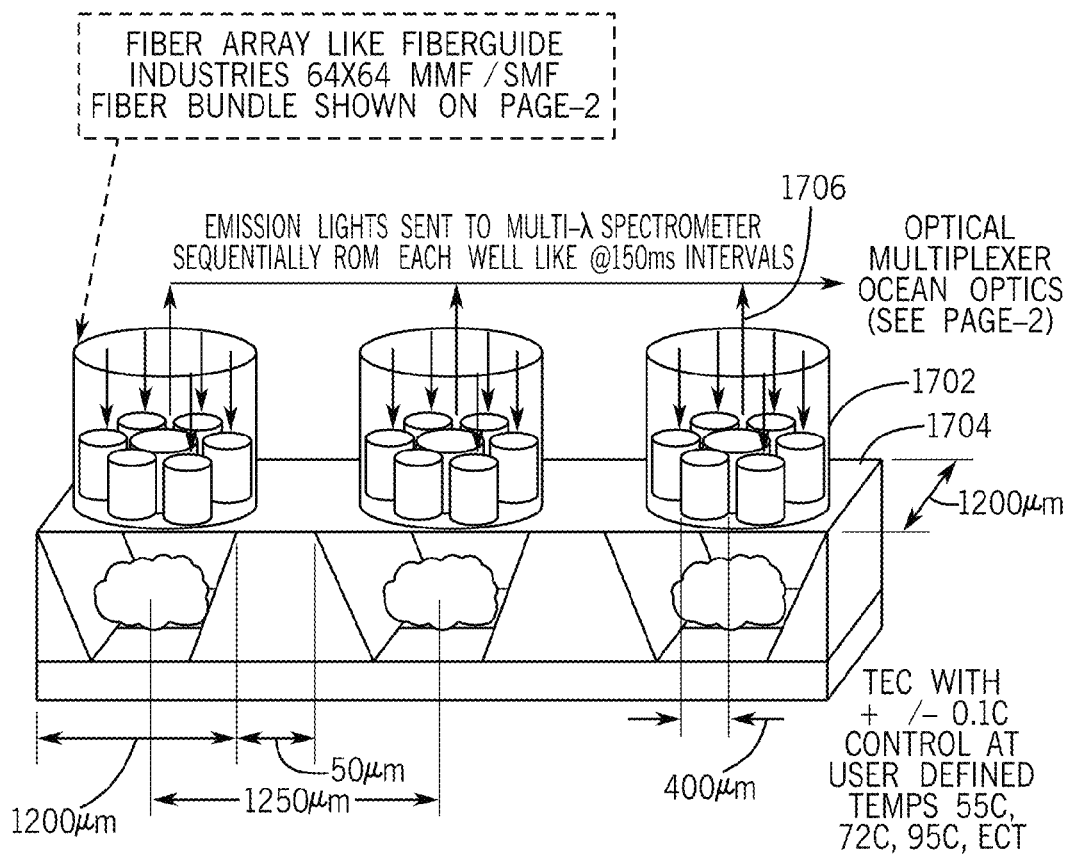
FIG. 17A depicts another apparatus of the present invention comprising an array of thermo-controllable units optically linked to an optical system.
Figure 17B:
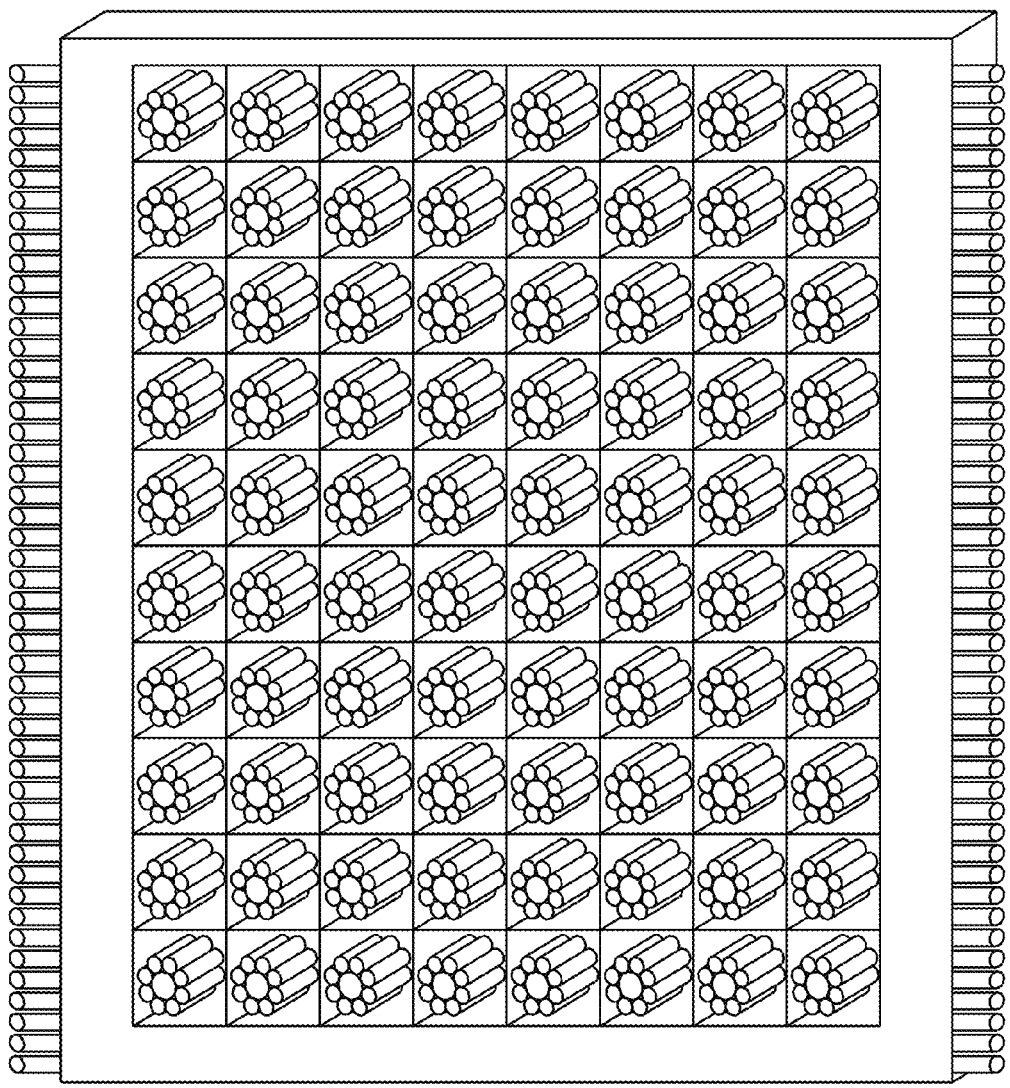
FIG. 17B depicts a top view of fiber bundle with localized 8-λ excitation light MMF and single 1 mm MMF for 8-λ different emission lights in mixed format. This is an MMF bundled fiber sub-assembly with all central emission MMF fiber goes through AWG and rest of the excitation to the sides.
Figure 18:
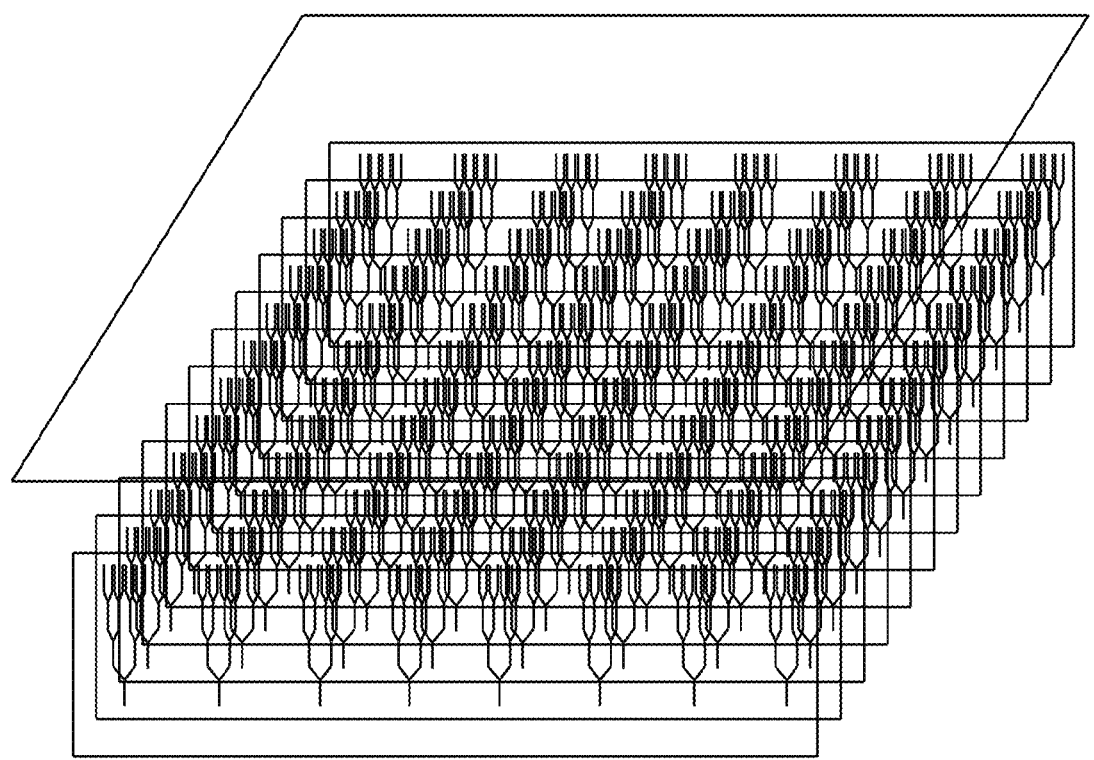
FIG. 18 depicts a 12×8 fiber array each having 1×8 channel and 18 mm long DE-MUX AWG for passive low loss emission light separation with real time analysis capability of all emissions simultaneously from a 16×96 well chip. The spectrum can be resolved and analyzed by EMCCD.

Another exemplary optical system of the present invention is depicted in FIG. 17. An array of fibers 1702 is employed to direct a plurality of excitation beams of the same or different wavelengths to a micro well 1704 on a chip. The fibers within the array can be arranged in a circular configuration as shown in FIG. 17A or any other convenient configurations. The optical signals coming from the reactants in the micro well is then collected and transported by fibers 1706 to a spectrometer. The spectrometer periodically and sequentially samples and analyzes the spectrum outputs of the fibers 1706. The optimal sampling frequency can be empirically determined. It may range from once every millisecond, to once every 150 milliseconds, and to once every 1500 milliseconds. This configuration is particularly suited for a range of spectroscopic applications because it permits the application of a wide range of excitation wavelengths to a reaction sample being examined. As such, the configuration supports analyses of fluorescence, chemiluminescence, scintillation, bioluminescence, and time-resolved applications without the need for frequent re-alignment of the excitation sources that provide the appropriate excitation wavelengths.

Figure 19:
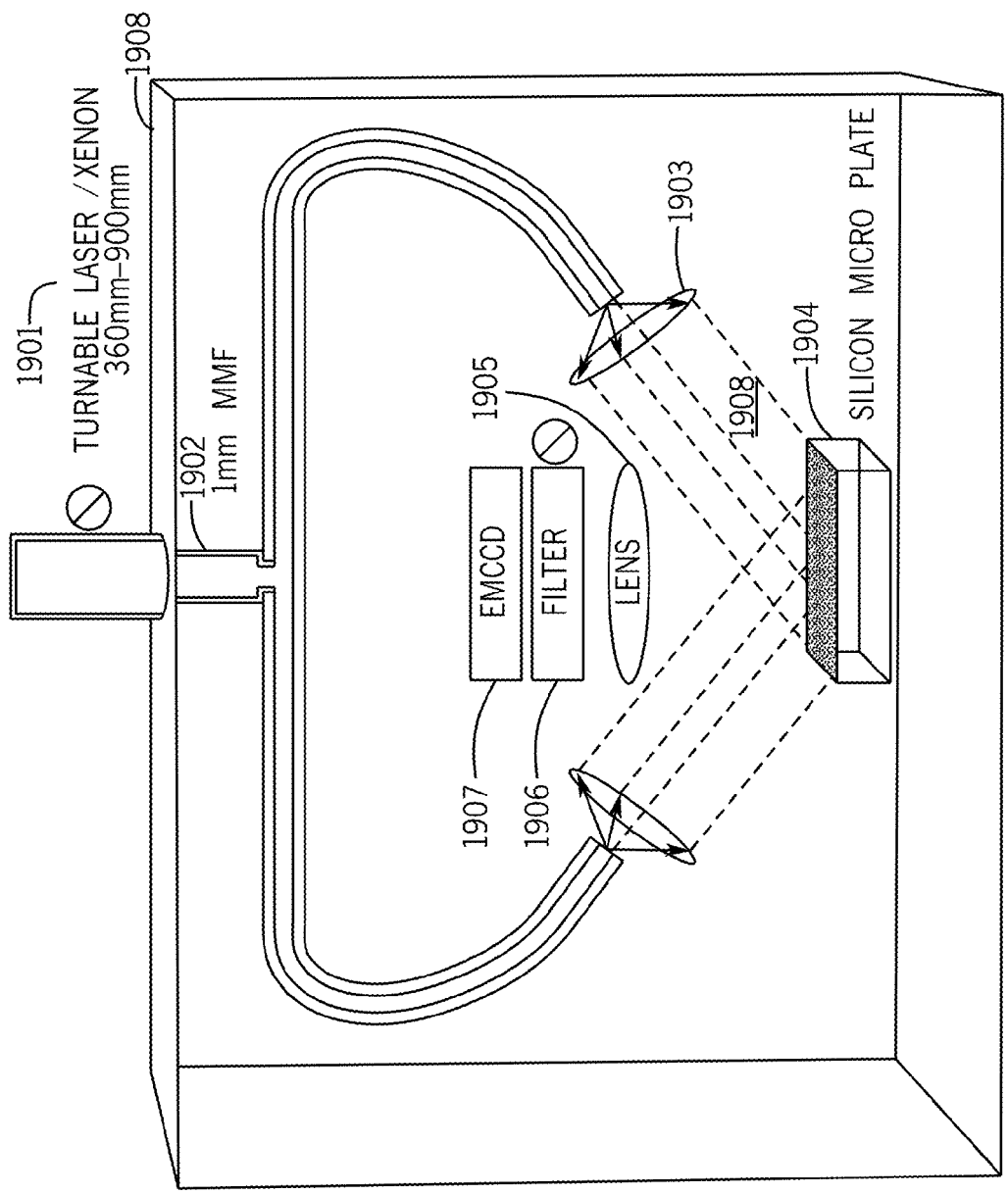
FIG. 19 depicts another apparatus of the present invention comprising an array of thermo-controllable units optically linked to an optical system.

FIG. 19 depicts another exemplary optical system of the present invention. In this system, optical fibers 1902 and beam collimators 1903 connected to an excitation source 1901 are employed to illuminate all the micro-wells on a chip 1904. The excitation source can be high power tunable lasers or Xenon lamps. The optical fibers 1902 are typically multi-mode fibers (MMF) of one millimeter diameter. The collimated beams from the excitation source preferably provide uniform energy distribution across all the micro wells in the chip. The optical signals coming from the micro wells on the silicon micro-plate are collimated by a lens 1905 and are passed through a tunable filter 1906 to an electron-multiplying charge-coupled device (EMCCD) for spectrum analysis. All of the elements including the optical fibers 1902, collimating lens 1903 and 1905, silicon microplate 1904, tunable filter 1906 and EMCCD 1907, are enclosed in a highly protected dark housing 1908. This particular embodiment offers a low cost solution for monitoring the progress and/or results of chemical reactions taking place in micro wells fabricated on a chip.

Preparation of the Subject Chips

The chips of the present invention can be fabricated using techniques well established in the Integrated Circuit (IC) and Micro-Electro-Mechanical System (MEMS) industries. The fabrication process typically proceeds with selecting a chip substrate, followed by using appropriate IC processing methods and/or MEMS micromachining techniques to construct and integrate various components.

Chip Substrate:

Several factors apply to the selection of a suitable chip substrate. First, the substrate must be a good thermal conductor. A good thermal conductor generally has a thermal conductivity value higher than 1 $W/m^{-1}K^{-1}$, preferably higher than 100 $W/m^{-1}K^{-1}$, more preferably higher than 140 $W/m^{-1}K^{-1}$. Whereas the material's thermal conductivity may be 250 $W/m^{-1}K^{-1}$ or higher, it usually does not exceed 500 $W/m^{-1}K^{-1}$. Second, the substrate must be relatively inert and chemically stable. Such substrate generally exhibits a low level of propensity to react with the reaction samples employed in the intended application. Moreover, the materials should also be selected based upon the ability or feasibility to integrate the thermal control elements onto or adjacent to them. A variety of materials meet these criteria. Exemplary materials include but are not limited to metalloids or semiconductors, such as silicon, silicates, silicon nitride, silicon dioxide, gallium phosphide, gallium arsenide, or any combinations thereof. Other possible materials are glass, ceramics (including crystalline and non-crystalline silicate, and non-silicate-based ceramics), metals or alloys, composite polymers that contain dopants (e.g., aluminum oxide to increase thermal conductivity), or any of a range of plastics and organic polymeric materials available in the art.

Fabrication Process:

Fabrication of the subject chips can be performed according to standard techniques of IC-processing and/or MEMS micromachining. Typically, the subject chips are fabricated as multi-layer structures. The process generally proceeds with constructing the bottom layer. Then a combination of techniques including but not limited to photolithography, chemical vapor or physical vapor deposition, dry or wet etching are employed to build structures located above or embedded therein. Vapor deposition, for example, enables fabrication of an extremely thin and uniform coating onto other materials, whereas etching allows for mass production of larger chip structures. Other useful techniques such as ion implantation, plasma ashing, bonding, and electroplating can also be employed to improve the surface properties of the chips or to integrate various components of the chips. The following details the fabrication process with reference to the exemplary chip designs depicted in the figures. The same general process and the apparent variations thereof are applicable to fabricate any of the subject chips described herein.

Figure 5:
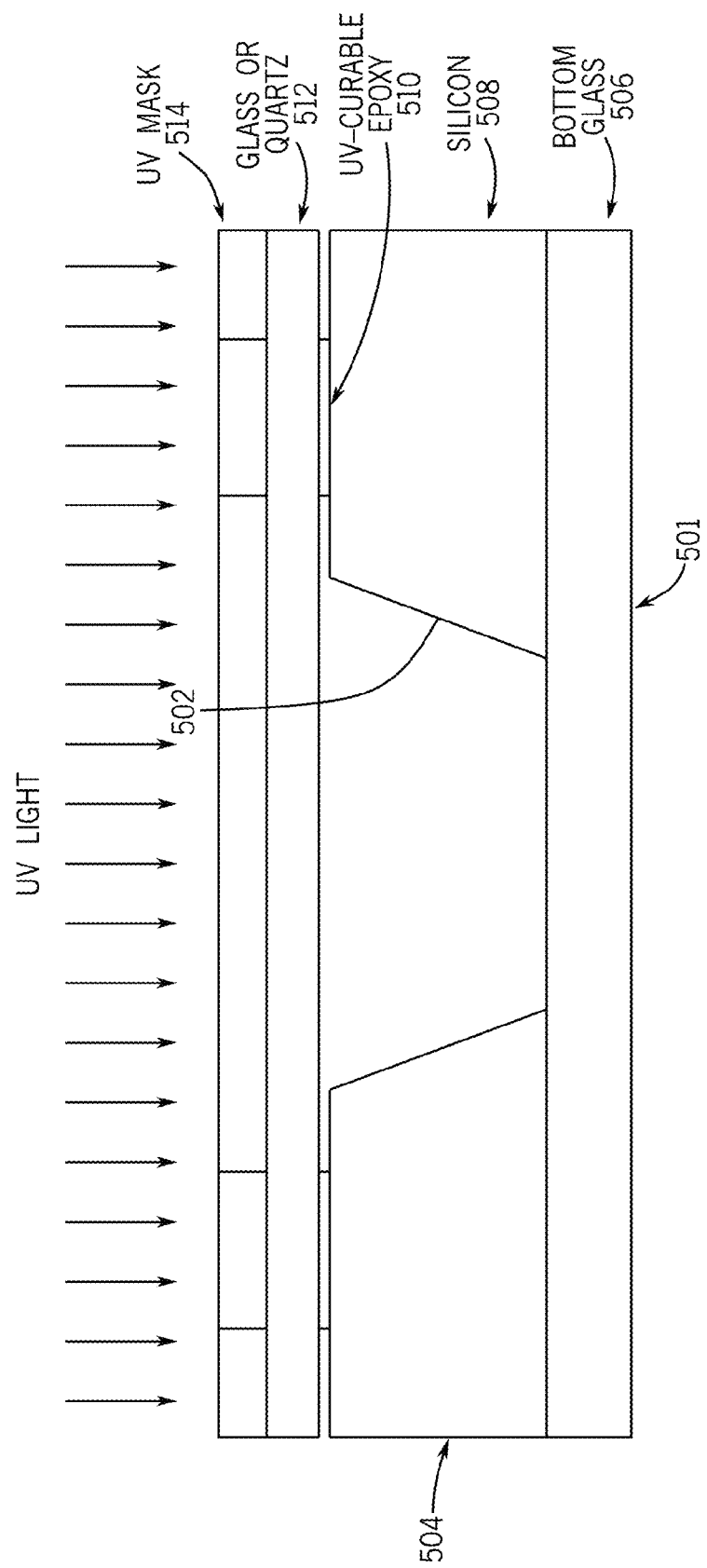
FIG. 5 depicts one illustrative chip design 501 having a sealed micro well. The micro well is sealed by first applying a UV-curable epoxy along the peripheral dimensions that defines the open surface of the micro well, followed by laying a photo mask that allows penetration of UV light along the peripheral dimensions, and then curing the epoxy using the UV light.

FIG. 5 is a cross-section of an exemplary chip design 501. In this embodiment, the micro well 502 is embedded within a body 504 which is made up of first and second (or bottom and top) layers of substrates 506 and 508, respectively. The process begins with providing a first layer of substrate which is generally a heat resistant material such as glass, Pyrex wafer, or any other suitable materials described herein or known in the art. The next step is to create the micro well 502 that forms the basis of the thermo-controllable unit. The micro well is generally disposed within the second layer 508 that is typically a silicon wafer. The silicon wafer may go through several processing steps prior to being attached to the first layer. For example, the silicon wafer may be attached to a layer of photoresist to render the surface more susceptible to chemical etching after exposure to UV light during the process of photolithography. The layer of photoresist defines, by precise alignment of the photo-mask, the size and location of the micro well that is to be formed by a subsequent etching step. The silicon wafer is then etched by a variety of means known in the art to form the well cavity. A commonly practiced etching technique involves the use of chemicals, e.g., potassium hydroxide (KOH), which removes the silicon wafer to form the desired shape.

Figure 6A:
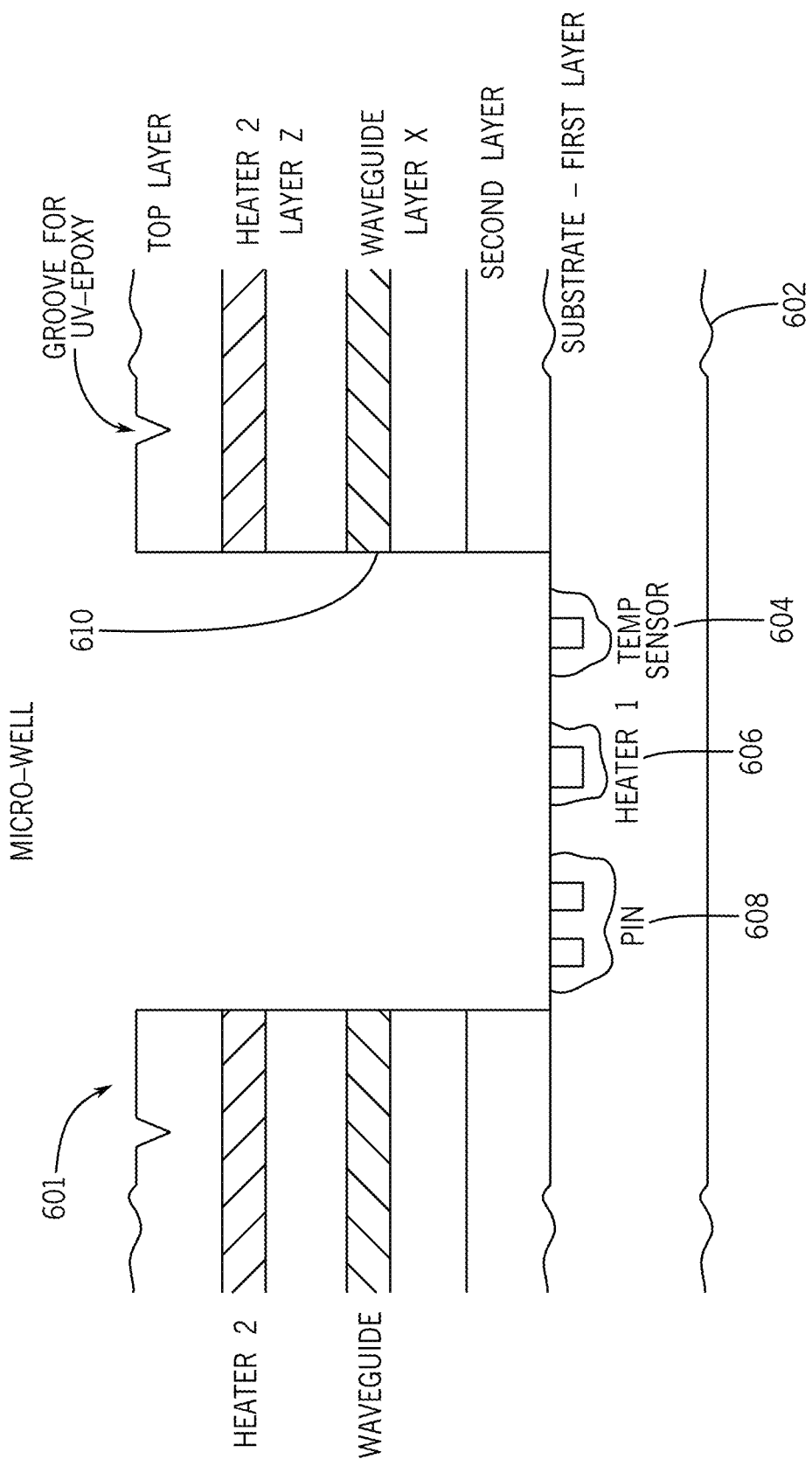
FIG. 6A is a schematic longitudinal cross sectional view of an exemplary chip design according to the present invention. The chip comprises several layers of materials, including a substrate layer fabricated therein a temperature sensor 604, a first heater 606, a photon-sensing device P-I-N diode 608. A waveguide 610, and a second heater are fabricated in the upper layers. The top layer comprises etched-in grooves for placement of epoxy for purpose of sealing the micro well.
Figure 7:
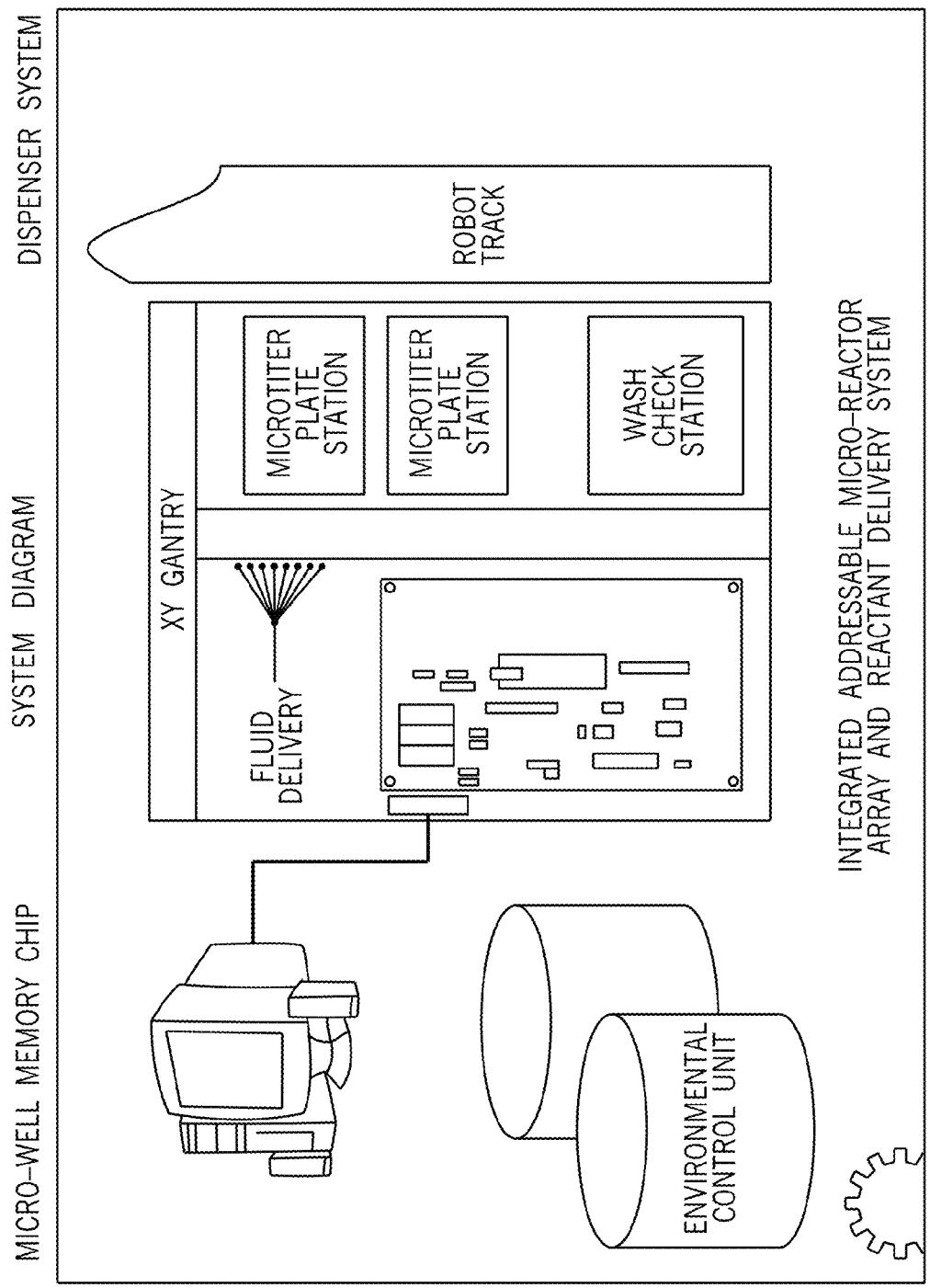
FIG. 7 is a schematic diagram showing different components of the overall analysis system.
Figure 11:
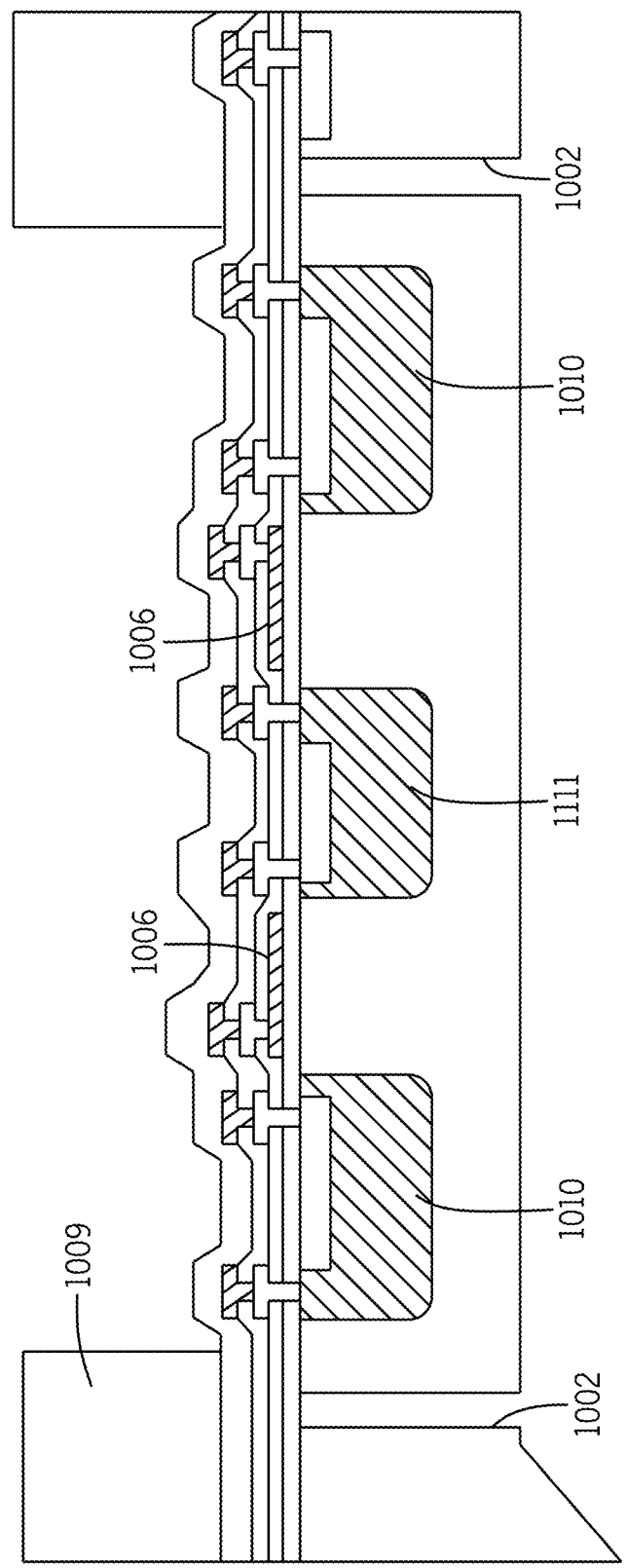
FIG. 11 is a schematic longitudinal cross sectional view along the cutting line IV shown in FIG. 8.
Figure 12:
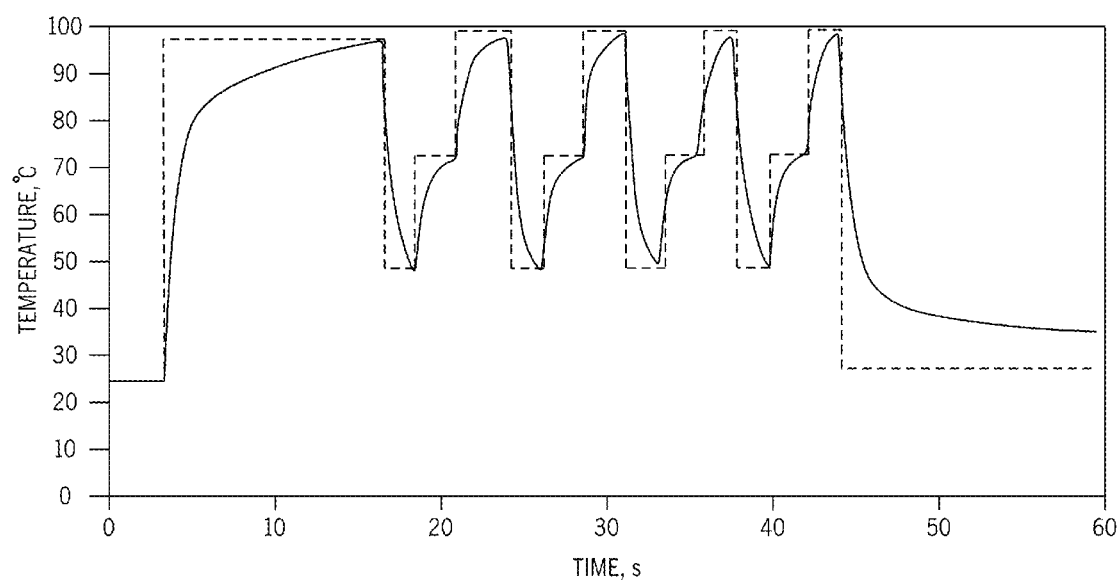
FIG. 12 depicts a typical thermal cycling profile using an exemplary chip described herein.

The heating element described herein can be deposited onto the interior surface of the micro well (see, e.g., FIGS. 6A and 11). The micro-heaters, for example, may be arranged to surround the micro well wall, or form the base of the micro well. The micro-heater and the fluid contained in the well can be isolated electrically and chemically from each other by an insulating or protective coating. Coating is particularly preferable in case of metal heating element that may be prone to corrosion and/or electrophoresis of the sample components during operation with fluid samples. A variety of protective coatings are available in the art, including those made of, e.g., $SiO_2$, $Si_3N_4$, and Teflon. Where the heating element is indium tin oxide, it is preferable to use glass (e.g. on borosilicate glass), quartz, or the like material as the adhesion layer before depositing it into the micro well.

Integrated circuitry that supports the operations of the heating element and/or the temperature sensor can also be implanted into the well or onto the exterior part of the silicon layer by a suitable IC-processing technique described herein or known in the art.

The second layer of silicon 508 in FIG. 5 or other suitable substrate material can be attached to the first glass layer in one of several ways. Anodic bonding can be used when the materials employed are compatible with the bonding requirements. Alternatively, a polymeric bonding compound such as benzocyclobutene (BCB) (available from Dow Chemical) can be applied to adhere one layer onto the next. In addition, the two layers of substrates can be fused together by extensive heating under high temperatures.

FIG. 6 and FIGS. 8-11 depict other exemplary chip designs 601 in which the first layer is made of silicon or the like material. In FIGS. 6 and 11, the temperature sensors 604 and 1111, heating elements 606 and 1006, and photo-sensing elements 608 and 1010 are fabricated in the first layer using methods described above or other methods illustrated in the pending application Ser. No. 10/691,036, the content of which is incorporated by reference in its entirety.

To enhance the detection and sensing capabilities of the chip, additional layers of sensing structures such as waveguides 610 are fabricated. The waveguides are constructed to channel light beams emitted from one or multiple micro wells through a side wall of the micro well 610. While it may be preferable to couple one waveguide to a single micro well to effect separate detection of light signals emitted from individual wells, channeling signals from multiple wells are possible by adjusting the excitation light beam. For instance, the incoming light can be synchronized in or out of phase with light signals collected from other waveguides such that multiple pulses of light beams of known wavelengths and intensities arrive at different micro wells within predetermined time frames. The sensor reading associated with that particular light pulse is then monitored with appropriate post processing. The materials with which the waveguides are fabricated are determined by the wavelength of the light being transmitted. Silicon dioxide is suitable for transmitting light beams of a wide spectrum of visible wavelengths. Silicon and polysilicon are applicable for guiding infra-red wavelengths. Those skilled in the art will know of other materials suitable for constructing waveguide. To achieve the desired polarization states, waveguides with appropriate integral gratings can be constructed using standard MEMS micromachining techniques.

The chip depicted in FIG. 6A also contains a top layer micro-heater. The top layer heater provides an additional source of heat energy to effect a rapid thermal cycling. It may also serve as a physical barrier to prevent evaporation of the reaction reagents applied to the micro well. To further minimize evaporation, the top layer heater can be maintained at a higher temperature, usually a few Celsius degrees higher relative to the bottom heater. The type of heater to be placed on the upper surface will depend on the intended use of the chip. Indium tin oxide heater is generally preferred because it is transparent to visible light. When deposited on glass and applied to the top of the chip, light emitted from the micro well can still pass through and be detected by a photon-sensing element.

Once the micro wells of the subject chips are fabricated, their surface properties can be improved to suit the particular application. Where large surface area is desired, the wall of the micro well may be further etched by, e.g., a plasma etcher to obtain very fine dendrites of silicon, commonly referred to as "black silicon". The presence of black silicon can dramatically increase the effective heating surface area. The black silicon fabricated at the base of the micro well may also serve as an anchor for photon-sensing devices, temperature sensors and other control elements.

As discussed in the sections above, a micro well of high inner surface to volume ratio may be coated with materials to reduce the possibility that the reactants contained therein may interact with the inner surfaces of the well. The choice of methods for applying the coating materials will depend on the type of coating materials that is used. In general, coating is carried out by directly applying the materials to the micro well followed by washing the excessive unbound coating material. Certain coating materials can be cross-linked to the surface via extensive heating, radiation, and by chemical reactions. Those skilled in the art will know of other suitable means for coating a micro well fabricated on chip, or will be able to ascertain such, without undue experimentation.

The surface of the micro well can further be altered to create adsorption sites for reaction reagents. One skilled in the art will appreciate that there are many ways of creating adsorption sites to immobilize chemical or biological reactants. For instance, a wealth of techniques are available for directly immobilizing nucleic acids and amino acids on a chip, anchoring them to a linker moiety, or tethering them to an immobilized moiety, via either covalent or non-covalent bonds (see, e.g., Methods Mol. Biol. Vol. 20 (1993), Beier et al., Nucleic Acids Res. 27:1970-1-977 (1999), Joos et al., Anal. Chem. 247:96-101 (1997), Guschin et al., Anal. Biochem. 250:203-211 (1997)).

The subject chips can be further modified to contain one or more grooves on the top, or at the bottom side of the chip (see, e.g., FIGS. 6A and 9). Grooves are generally fabricated by etching the bottom side silicon wafer. Back-side etching can be carried out before or after formation of the micro well.

Sealing Process

In most of the applications, sealing the micro wells is desirable to prevent evaporation of liquids and thus maintains the preferred reaction concentrations throughout the thermal cycling. Accordingly, the present invention provides a technique for sealing an array of micro wells. The design of the subject sealing technique takes several factors into consideration. First, the technique should be amenable to high throughout processing of a large quantity of micro wells. Second, the method should permit selective sealing of individual micro wells. As such, the method can yield chips comprising open micro wells interspersed among sealed micro wells in any desired pattern or format. As mentioned above, chips having both open and sealed micro wells are particularly desirable. The open and/or unfilled wells not only allow passive dissipation of heat, but also reduce heat transfer between the neighboring micro wells.

A preferred method of sealing an array of micro wells containing at least one open well. The method comprises the steps of (a) applying a radiation-curable adhesive along peripheral dimensions defining the open surface of the at least one open micro well; (b) placing a cover to encompass the peripheral dimensions that define the open surface of the at least one open micro well that is to be sealed; and (c) exposing the array to a radiation beam to effect the sealing.

As used herein, "radiation-curable adhesive" refers to any composition that cures and bonds to the adhering surface upon exposure to a radiation beam without the need of extensive heating. "Radiation beam" refers to electromagnetic waves of energy including, in an ascending order of frequency, infrared radiation, visible light, ultraviolet (VU) light, X-rays, and gamma rays. A vast number of radiation-curable adhesive are commercially available (see, e.g., a list of companies selling radiation-curable adhesive and radiation systems from ThomasNet®'s worldwide web site). They include a diversity of acrylics, acrylates, polyurethanes (PUR), polyesters, vinyl, vinyl esters, and a vast number of epoxies that are curable by radiation beams at various frequencies. These and other radiation-curable materials are supplied commercially in form of liquid, or solid such as paste, powder, resin, and tape.

The choice of radiation-curable adhesive will dependent on the materials made up the surfaces to be adhered. The aforementioned classes of adhesive are suited for adhering the chip substrate to the cover which can be made of a range of materials. For instance, acrylics and epoxies are applicable for radiation-sealing any two surfaces, made of any one of the materials selected from glass, ceramics, metalloids, semiconductors (e.g., silicon, silicates, silicon nitride, silicon dioxide, quartz, and gallium arsenide), plastics, and other organic polymeric materials. Radiation-curable materials exhibiting the properties of low use temperature and rapid curing time are particularly desirable for sealing the subject chips. These materials allow for a rapid sealing to avoid radiation damages to the chemical or biological reagents contained in the chips.

Figure 25:
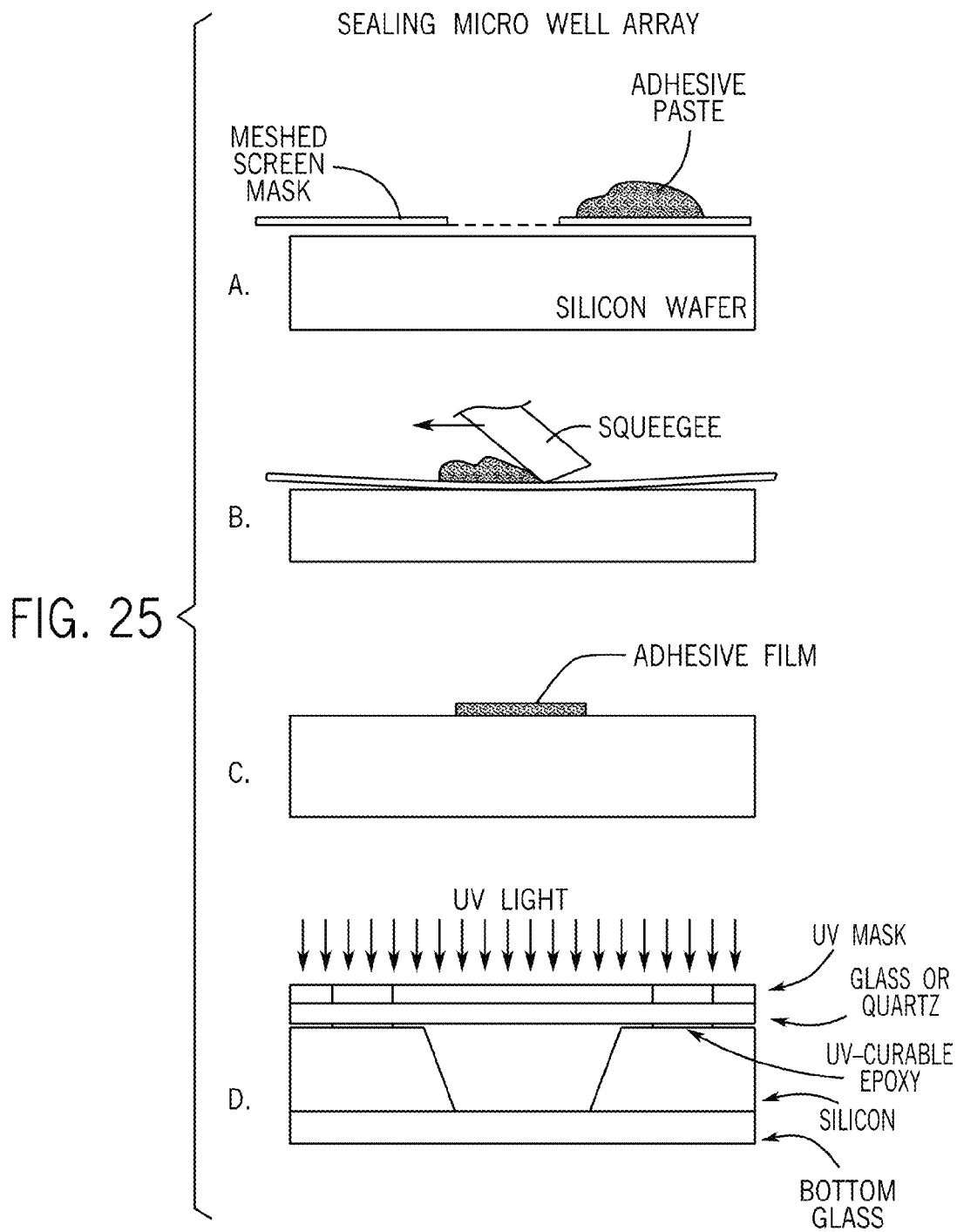
FIG. 25 depicts an exemplary method for sealing the subject micro well.

The radiation-curable adhesive can be applied by any mechanical means along the peripheral dimensions that define the open surface of a micro well. The "peripheral dimensions" can be the boundaries on the chip substrate or on the cover. In either case, the peripheral dimensions become bonded to the respective adhering surface, the substrate or the cover, upon curing the adhesive. The radiation-curable adhesive can be smeared, printed, dispensed, or sprayed onto the peripheral dimensions using any suitable tools. Preferred mechanical means yields a uniform layer of adhesive on the peripheral dimensions. One way to provide a uniform distribution is to apply the adhesive directly onto the peripheral dimensions of an open well using a squeegee over a meshed screen mask (see, e.g., FIG. 25). Alternatively, the radiation-curable adhesive can be applied directly onto the cover that has been marked with the peripheral dimensions using the meshed screen mask. A uniform layer of adhesive is achieved upon removal of the mask.

Upon application of the radiation-curable adhesive, a cover is placed on the micro well to encompass the peripheral dimensions that define the open surface of the well. Suitable covers are generally made of materials that permit passage of a radiation beam. Preferred covers are fabricated with transparent materials such as glass, quartz, plastic, any suitable organic polymeric materials known to those skilled in the art, or any combinations thereof.

Sealing a covered micro well is carried out by exposing the well to a radiation beam. Depending on the type of adhesive selected, the radiation beam may come from a conventional incandescent source, a laser, a laser diode, UV-bulb, an X-ray machine or gamma-ray machine, or the like. Where desired, radiation beam from the radiation source is permitted to reach only selected locations on the micro well array so that only certain selected wells are to be sealed. A selective sealing is often achieved by using a photo-mask patterned with the locations of the micro wells. The photo-mask is provided with transparent locations and opaque locations that correspond to the micro wells that are to be sealed and those that are to remain open, respectively. The radiation beam passes freely through the transparent regions but is reflected from or absorbed by the opaque regions. Therefore, only selected micro wells are exposed to light and hence sealed by curing the adhesive. In one embodiment, the photo-mask is patterned such that no two adjoining open micro wells are to be sealed. In another embodiment, the photo-mask is patterned such that the resulting micro well array contains alternating sealed and unsealed wells. One skilled in the art can fashion an unlimited number of photo-masks with any patterns to yield chips containing open and sealed micro wells in any format. Methods for manufacturing such photo-masks are well established in the art and hence are not detailed herein.

Uses of the Subject Chip and Other Devices of the Present Invention

The subject chips have a wide variety of uses in chemical and biological applications where controllable temperatures are desired.

In one embodiment, the subject chips can be used to vary and/or maintain temperature of a reaction sample. Varying and/or maintaining temperature of a reaction sample are required in a wide range of circumstances including but not limited to discerning protein-protein interaction, examining DNA or RNA hybridization, and performing enzymatic reaction. The method involves placing the reaction sample into a micro well fabricated in a chip that is in thermal contact with a heating element, and applying a voltage to the heating element.

In another embodiment, the subject chips are used for conducting a chemical reaction that involves a plurality of reaction samples and, requires cycling at least two temperature levels. The process involves (a) providing a chip comprising an array of thermo-controllable units as described herein; (b) placing the plurality of reaction samples into the thermo-controllable units of the chip; and (c) controlling the heating element to effect cycling at least two temperature levels.

As used herein, the term "chemical reaction" refers to any process involving a change in chemical properties of a substance. Such process includes a vast diversity of reactions involving biological molecules such as proteins, glycoproteins, nucleic acids, and lipids, or inorganic chemicals, or any combinations thereof. The chemical reaction may also involve interactions between nucleic acid molecules, between proteins, between nucleic acid and protein, between protein and small molecules. Where the process is catalyzed by an enzyme, it is also referred to as "enzymatic reaction."

The subject chips and other apparatus are particularly useful in conducting enzymatic reactions because most enzymes function under only certain temperatures. Representative enzymatic reactions that are particularly temperature dependent include but are not limited to nucleic acid amplification, quantitative polymerase chain reaction (qPCR), nucleic acid sequencing, reverse transcription, and nucleic acid ligation.

Practicing the subject method generally proceeds with placing the reaction sample into a micro well of the subject chip that is in thermal contact with a heating element. Where desired, the reaction sample can be applied by a dispensing system operatively coupled to the subject chip. A variety of dispensing instruments, ranging from manually operated pipettes to automated robot systems are available in the art. Preferred dispensing instruments are compatible to the particular format (e.g. 96-well) of the subjects chip.

To prevent evaporation of aqueous reaction samples, the samples can be applied to the micro well at or around dew point. As used herein, "dew point" refers to a temperature range where the droplet size does not change significantly. At dew point, an equilibrium is reached between the rate of evaporation of water from the sample droplet and the rate of condensation of water onto the droplet from the moist air overlying the chip. When this equilibrium is realized, the air is said to be saturated with respect to the planar surface of the chip. At one atmospheric pressure, the dew point is about 14° C. Accordingly, dispensing aqueous reaction samples is preferably carried out at a temperature no more than about 1° C. to about 5° C. degrees above dew point. As is apparent to one skilled in the art, dew point temperature increases as the external pressure increases. Therefore, where desired, one may dispense the reaction samples in a pressured environment to prevent evaporation.

In practice, controlling the heating element and hence the temperature of the reaction sample, is effected by processing a predetermined algorithm stored on a computer readable medium operatively linked to the heating element. In other aspects, the controlling step may involve processing sensor signals retrieved from a temperature sensor element that is operatively linked to a thermo-controllable unit based on protocols stored on a computer readable medium. This can be achieved by employing conventional electronics components for temperature control that may process either analog or digital signals. Preferably, the electronics components are run on a feedback control circuitry. They can control the temperature of one unit, but more often the temperature of multiple thermo-controllable units that collectively form one temperature zone. Where desired, the chemical reactions can take place in different thermo-controllable units located in different temperature zones. In certain embodiments, the temperatures of the different zones are separately controlled. The thermal cycling profile and duration will depend on the particular application in which the subject chip is to be employed.

Nucleic Acid Amplification:

The chips of the present invention provide a cost-effective means for amplifying nucleic acids. Unlike the conventional thermal cyclers, the subject chips are highly miniaturized, capable of performing rapid amplification of a vast number of target nucleic acids in small volume, and under independent thermal protocols.

As used herein, "nucleic acid amplification" refers to an enzymatic reaction in which the target nucleic acid is increased in copy number. Such increase may occur in a linear or in an exponential manner. Amplification may be carried out by natural or recombinant DNA polymerases such as Taq polymerase, Pfu polymerase, T7 DNA polymerase, Klenow fragment of E. coli DNA polymerase, and/or RNA polymerases such as reverse transcriptase.

A preferred amplification method is polymerase chain reaction (PCR). General procedures for PCR are taught in U.S. Pat. No. 4,683,195 (Mullis) and U.S. Pat. No. 4,683,202 (Mullis et al.). Briefly, amplification of nucleic acids by PCR involves repeated cycles of heat-denaturing the DNA, annealing two primers to sequences that flank the target nucleic acid segment to be amplified, and extending the annealed primers with a polymerase. The primers hybridize to opposite strands of the target nucleic acid and are oriented so that the synthesis by the polymerase proceeds across the segment between the primers, effectively doubling the amount of the target segment. Moreover, because the extension products are also complementary to and capable of binding primers, each successive cycle essentially doubles the amount of target nucleic acids synthesized in the previous cycle. This results in exponential accumulation of the specific target nucleic acids at approximately a rate of $2^n$, where n is the number of cycles.

A typical conventional PCR thermal cycling protocol comprises 30 cycles of (a) denaturation at a range of 90° C. to 95° C. for 0.5 to 1 minute, (b) annealing at a temperature ranging from 55° C. to 65° C. for 1 to 2 minutes, and (c) extension at 68° C. to 75° C. for at least 1 minute with the final cycle extended to 10 minutes. With the subject chips, the thermal cycling time can be drastically reduced because of, partly, the small reaction volume, the small heating mass, and the design of effective heat dissipation features.

A variant of the conventional PCR is a reaction termed "Hot Start PCR". Hot Start PCR techniques focus on the inhibition of polymerase activity during reaction preparation. By limiting polymerase activity prior to PCR cycling, non-specific amplification is reduced and the target yield is increased. Common methods for Hot Start PCR include chemical modifications to the polymerase (see, e.g., U.S. Pat. No. 5,773,258), inhibition of the polymerase by a polymerase-specific antibody (see, e.g., U.S. Pat. No. 5,338,671), and introduction of physical barriers in the reaction site to sequester the polymerase before the thermal cycling takes place (e.g., wax-barrier methods). The reagents necessary for performing Hot Start PCR are conveniently packaged in kits that are commercially available (see, e.g., Sigma's JumpStart Kit).

Another variant of the conventional PCR that can be performed with the subject chips is "nested PCR" using nested primers. The method is preferred when the amount of target nucleic acid in a sample is extremely limited for example, where archival, forensic samples are used. In performing nested PCR, the nucleic acid is first amplified with an outer set of primers capable of hybridizing to the sequences flanking a larger segment of the target nucleic acid. This amplification reaction is followed by a second round of amplification cycles using an inner set of primers that hybridizes to target sequences within the large segment.

The subject chips can be employed in reverse transcription PCR reaction (RT-PCR). RT-PCR is another variation of the conventional PCR, in which a reverse transcriptase first coverts RNA molecules to double stranded cDNA molecules, which are then employed as the template for subsequent amplification in the polymerase chain reaction. In carrying out RT-PCR, the reverse transcriptase is generally added to the reaction sample after the target nucleic acids are heat denatured. The reaction is then maintained at a suitable temperature (e.g., 30-45° C.) for a sufficient amount of time (e.g., 5-60 minutes) to generate the cDNA template before the scheduled cycles of amplification take place. Such reaction is particularly useful for detecting the biological entity whose genetic information is stored in RNA molecules. Non-limiting examples of this category of biological entities include RNA viruses such as HIV and hepatitis-causing viruses. Another important application of RT-PCR embodied by the present invention is the simultaneous quantification of biological entities based on the mRNA level detected in the test sample. One of skill in the art will appreciate that if a quantitative result is desired, caution must be taken to use a method that maintains or controls for the relative copies of the amplified nucleic acids.

Methods of "quantitative" amplification of nucleic acids are well known to those of skill in the art. For example, quantitative PCR (qPCR) can involve simultaneously co-amplifying a known quantity of a control sequence using the same primers. This provides an internal standard that may be used to calibrate the PCR reaction. Other ways of performing qPCR are available in the art and are detailed in the section "Detection of Amplified Target Nucleic Acids" below.

The subject chips can also be employed to form ligase chain polymerase chain reaction (LCR-PCR). The method involves ligating the target nucleic acids to a set of primer pairs, each having a target-specific portion and a short anchor sequence unrelated to the target sequences. A second set of primers containing the anchor sequence is then used to amplify the target sequences linked with the first set of primers. Procedures for conducting LCR-PCR are well known to artisans in the field, and hence are not detailed herein (see, e.g., U.S. Pat. No. 5,494,810).

Nucleic acid amplification is generally performed with the use of amplification reagents. Amplification reagents typically include enzymes, aqueous buffers, salts, primers, target nucleic acid, and nucleoside triphosphates. Depending upon the context, amplification reagents can be either a complete or incomplete amplification reaction mixture.

The choice of primers for use in nucleic acid amplification will depend on the target nucleic acid sequence. Primers used in the present invention are generally oligonucleotides, usually deoxyribonucleotides several nucleotides in length, that can be extended in a template-specific manner by the polymerase chain reaction. The design of suitable primers for amplifying a target nucleic acid is within the skill of practitioners in the art. In general, the following factors are considered in primer design: a) each individual primer of a pair preferably does not self-hybridize; b) the individual pairs preferably do not cross-hybridize; and c) the selected pair must have the appropriate length and sequence homology in order to anneal to two distinct regions flanking the nucleic acid segment to be amplified. However, not every nucleotide of the primer must anneal to the template for extension to occur. The primer sequence need not reflect the exact sequence of the target nucleic acid. For example, a non-complementary nucleotide fragment may be attached to the 5' end of the primer with the remainder of the primer sequence being complementary to the target. Alternatively, non-complementary bases can be interspersed into the primer, provided that the primer sequence has sufficient complementarily with the target for annealing to occur and allow synthesis of a complementary nucleic acid strand.

For a convenient detection of the amplified nucleotide acids resulting from PCR or any other nucleic acid amplification reactions described above or known in the art, primers may be conjugated to a detectable label. Detectable labels suitable for use in the present invention include any composition detectable by spectroscopic, photochemical, biochemical, immunochemical, electrical, optical or chemical means. A wide variety of appropriate detectable labels are known in the art, which include luminescent labels, enzymatic or other ligands. In preferred embodiments, one will likely desire to employ a fluorescent label or an enzyme tag, such as digoxigenin, B-galactosidase, urease, alkaline phosphatase or peroxidase, avidin/biotin complex.

The labels may be incorporated by any of a number of means well known to those of skill in the art. In one aspect, the label is simultaneously incorporated during the amplification step. Thus, for example, PCR with labeled primers or labeled nucleotides can provide a labeled amplification product. In a separate aspect, transcription reaction in which RNA is converted into DNA, using a labeled nucleotide (e.g. fluorescein-labeled UTP and/or CTP) or a labeled primer, incorporates a detectable label into the transcribed nucleic acids.

The primer pairs used in this invention can be obtained by chemical synthesis, recombinant cloning, or a combination thereof. Methods of chemical polynucleotide synthesis are well known in the art and need not be described in detail herein. One of skill in the art can use the target sequence to obtain a desired primer pairs by employing a DNA synthesizer or ordering from a commercial service.

Nucleic acid amplification requires a target nucleic acid in a buffer compatible with the enzymes used to amplify the target. The target nucleic acid used for this invention encompasses any reaction samples suspected to contain the target sequence. It is not intended to be limited as regards to the source of the reaction sample or the manner in which it is made. Generally, the test sample can be biological and/or environmental samples. Biological samples may be derived from human, other animals, or plants, body fluid, solid tissue samples, tissue cultures or cells derived therefrom and the progeny thereof, sections or smears prepared from any of these sources, or any other samples suspected to contain the target nucleic acids. Preferred biological samples are body fluids including but not limited to blood, urine, spinal fluid, cerebrospinal fluid, sinovial fluid, ammoniac fluid, semen, and saliva. Other types of biological sample may include food products and ingredients such as vegetables, dairy items, meat, meat by-products, and waste. Environmental samples are derived from environmental material including but not limited to soil, water, sewage, cosmetic, agricultural and industrial samples.

Preparation of nucleic acids contained in the test sample can be carried out according to standard methods in the art or procedures described. Briefly, DNA and RNA can be isolated using various lytic enzymes or chemical solutions according to the procedures set forth in Sambrook et al. ("Molecular Cloning: A Laboratory Manual"), or extracted by nucleic acid binding resins following the accompanying instructions provided by manufacturers' instructions.

The nucleic acid in the reaction sample can be cDNA, genomic DNA or viral DNA. However, the present invention can also be practiced with other nucleic acids, such as mRNA, ribosomal RNA, viral RNA. These nucleic acids may exist in a variety of topologies. For example, the nucleic acids may be single stranded, double-stranded, circular, linear or in form of concatamers. Those of skill in the art will recognize that whatever the nature of the nucleic acid, it can be amplified merely by making appropriate and well recognized modifications to the method being used.

Detection of Amplified Target Nucleic Acid:

Amplified nucleic acids present in the subject chips may be detected by a range of methods including but not limited to (a) forming a detectable complex by, e.g., binding the amplified product with a detectable label; and (b) electrophoretically resolve the amplified product from reactants and other components of the amplification reaction.

In certain embodiments, the amplified products are directly visualized with detectable label such as a fluorescent DNA-binding dye. Because the amount of the dye intercalated into the double-stranded DNA molecules is typically proportional to the amount of the amplified DNA products, one can conveniently determine the amount of the amplified products by quantifying the fluorescence of the intercalated dye using the optical systems of the present invention or other suitable instrument in the art. DNA-binding dye suitable for this application include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and the like.

In addition to various kinds of fluorescent DNA-binding dye, other luminescent labels such as sequence specific probes can be employed in the amplification reaction to facilitate the detection and quantification of the amplified product. Probe based quantitative amplification relies on the sequence-specific detection of a desired amplified product. Unlike the dye-based quantitative methods, it utilizes a luminescent, target-specific probe (e.g., TaqMan® probes)

resulting in increased specificity and sensitivity. Methods for performing probe-based quantitative amplification are well established in the art and are taught in U.S. Pat. No. 5,210,015.

The subject chips and the associated optical systems are particularly suited for conducting quantitative nucleic acid amplification. Accordingly, the present invention provides a method for monitoring the formation of a nucleic acid amplification reaction product, preferably in real time. In certain preferred embodiments, the amplified nucleic acids contained are directly monitored by the photon-sensing elements integrated into the chips. The photon-sensing element registers the intensities of the optical signals that are reflective of the amount of the amplified nucleic acids at any time being examined during the amplification reaction. The optical signals may be any kind of luminescent signals emitted upon exciting the labeled reactants with appropriate incident beams.

In another preferred embodiment, the amplified nucleic acids in the subject chips are detected by the subject optical systems operatively coupled to the chips. The optical systems are capable of transmitting appropriate excitation beams to the reactants in the amplification reactions, collecting and analyzing the emitted optical signals from the reactants. Preferably, the optical signals detected are indicative of the amount of amplified nucleic acid in the amplification reaction over a multiple-cycle period. In certain aspects, the optical system transmits excitation beams into the wells containing the reaction samples at a plurality of times during the amplification, and monitors the optical signals coming from the micro wells at each of the plurality of times. By analyzing the relative intensities of the optical signals, preferably over a multiple-cycle period, one can monitor quantitatively the progression of the amplification reaction. Typically, the optical signals being monitored are luminescent signals. In certain preferred aspects, detecting and/or monitoring the amplification products are performed without opening the micro well once the amplification is initiated.

Uses of Nucleic Acid Amplification and Detection Techniques of the Present Invention:

The subject methods of amplifying and detecting a target nucleic acid have broad spectrum of utility in, e.g. drug screening, disease diagnosis, phylogenetic classification, genotyping individuals, parental and forensic identification.

At a more fundamental level, amplification and detection of the target nucleic acids may be used in identification and quantification of differential gene expression between diseased and normal tissues, among different types of tissues and cells, amongst cells at different developmental stages or at different cell-cycle points, and amongst cells that are subjected to various environmental stimuli or lead drugs.

Other Chemical and Biological Applications:

The subject chips and other devices find utility in many other chemical and biological applications where controllable temperatures are desired. Such applications include a vast diversity of reactions such as redox reactions, hydrolysis, phosphorylation, and polymerization. Additional applications are directed to discerning interactions involving biological molecules such as proteins, glycoproteins, nucleic acids, and lipids, as well as inorganic chemicals, or any combinations thereof. The chemical reaction may also involve interactions between nucleic acid molecules, between nucleic acid and protein, between protein and small molecules The chemical reaction may take place outside a cell or inside a cell that is introduced into a micro well of the subject chip.

Of particular significance is the application in detecting the presence of a specific protein-protein interaction. Such application generally employs a proteinaceous probe and a target protein placed in a micro well in the subject chip.

In one aspect of this embodiment, the protein-protein interaction is between a target protein (i.e. an antigen) and an antibody specific for that target. In another aspect, the protein-protein interaction is between a cell surface receptor and its corresponding ligand. In yet another aspect, the protein-protein interaction involves a cell surface receptor and an immunoliposome or an immunotoxin; in other aspects, the protein-protein interaction may involve a cytosolic protein, a nuclear protein, a chaperon protein, or proteins anchored on other intracellular membranous structures.

The terms "membrane", "cytosolic", "nuclear" and "secreted" as applied to cellular proteins specify the extracellular and/or subcellular location in which the cellular protein is mostly, predominantly, or preferentially localized.

"Cell surface receptors" represent a subset of membrane proteins, capable of binding to their respective ligands. Cell surface receptors are molecules anchored on or inserted into the cell plasma membrane. They constitute a large family of proteins, glycoproteins, polysaccharides and lipids, which serve not only as structural constituents of the plasma membrane, but also as regulatory elements governing a variety of biological functions.

The reaction is typically performed by contacting the proteinaceous probe with a target protein under conditions that will allow a complex to form between the probe and the target. The conditions such as the reaction temperature, the duration of the reaction, the buffer conditions and etc., will depend on the particular interaction that is being investigated. In general, it is preferable to perform the reactions under physiologically relevant temperature and buffer conditions. Physiologically relevant temperatures range from approximately room temperature to approximately 37° C. This can be achieved by adjusting the heating element of the subject chips. Typically, a physiological buffer contains a physiological concentration of salt and at adjusted to a neutral pH ranging from about 0.6.5 to about 7.8, and preferably from about 7.0 to about 7.5. A variety of physiological buffers is listed in Sambrook et al. (1989) supra and hence is not detailed herein.

The formation of the complex can be detected directly or indirectly according standard procedures in the art or by methods describe herein. In the direct detection method, the probes are supplied with a detectable label and when a complex is formed, the probes emitted an optical signal distinct from that of the unreacted probes. A desirable label generally does not interfere with target binding or the stability of the resulting target-probe complex. As described above, a wide variety of labels suitable for such application are known in the art, most of which are luminescent probes. The amount of probe-target complexes formed during the binding reaction can be quantified by standard quantitative assays, or the quantitative methods using the optical systems described above.

Further illustration of the design and use of the chips according to this invention is provided in the Example section below. The example is provided as a guide to a practitioner of ordinary skill in the art, and is not meant to be limiting in any way.

EXAMPLE 1

Amplification of a target nucleic acid, namely a fragment of the G6PDH gene, is performed using a chip of the present invention. The reaction mixture contains G6PDH template, a pair of upstream and downstream primers specific for the template, dNTPs, and DNA polymerase.

Figure 20:
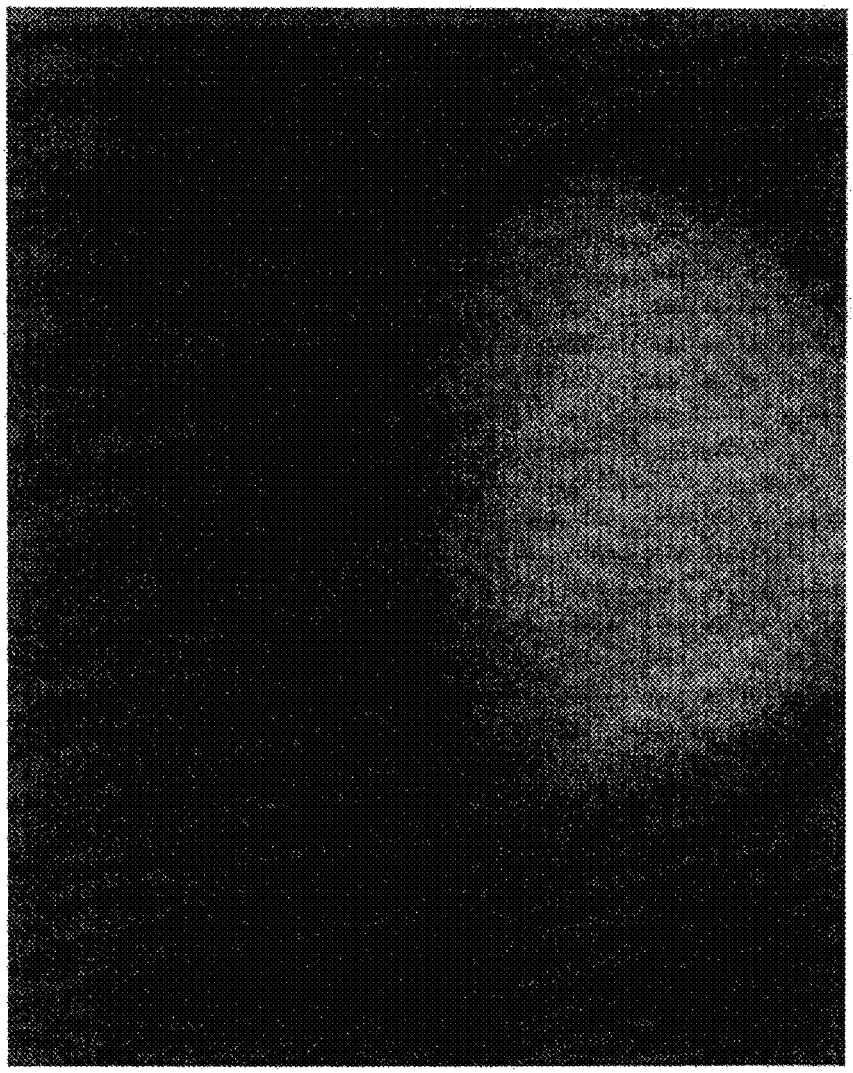
FIG. 20 depicts the SYBR Green-stained G6PDH gene products amplified using a chip of the present invention.
Figure 21:
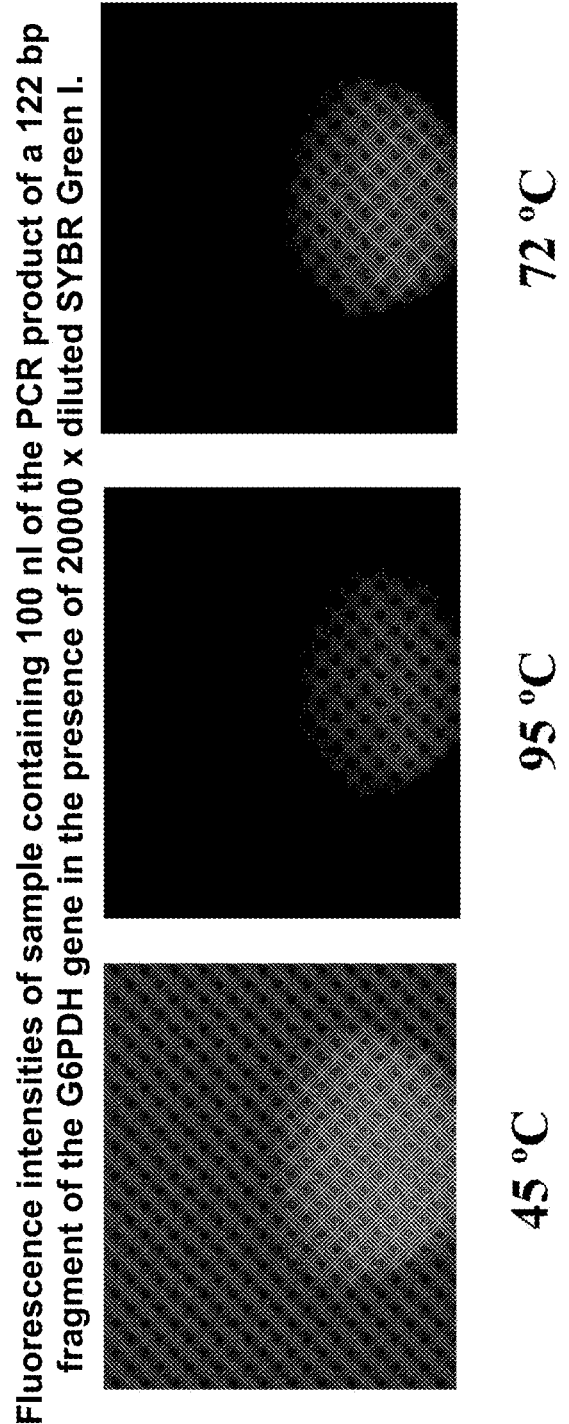
FIG. 21 depicts the SYBR Green staining of G6PDH gene products appeared at the three different thermal stages of one PCR cycle. The three stages are primer annealing at 45° C., denaturation of DNA at 95° C., and primer-dependent extension at 72° C.
Figure 22:
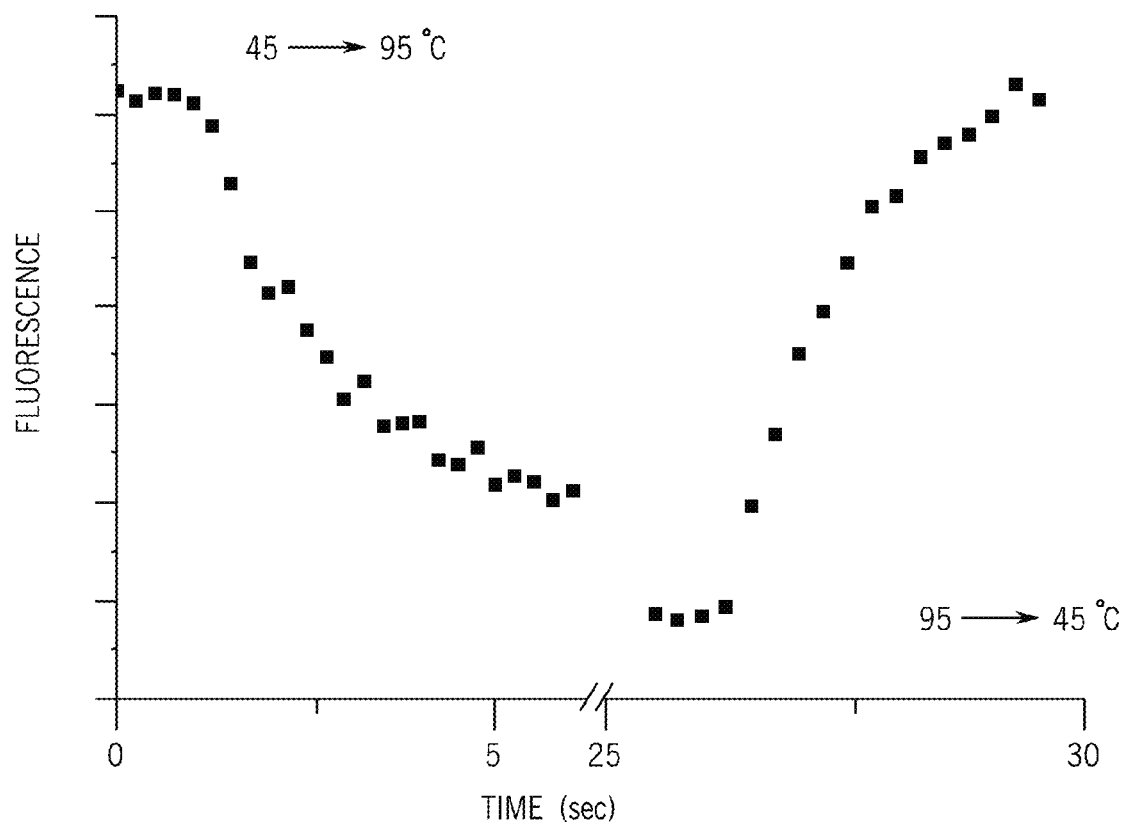
FIG. 22 depicts the amount of SYBR stain quantified throughout one complete thermal cycle.
Figure 23:
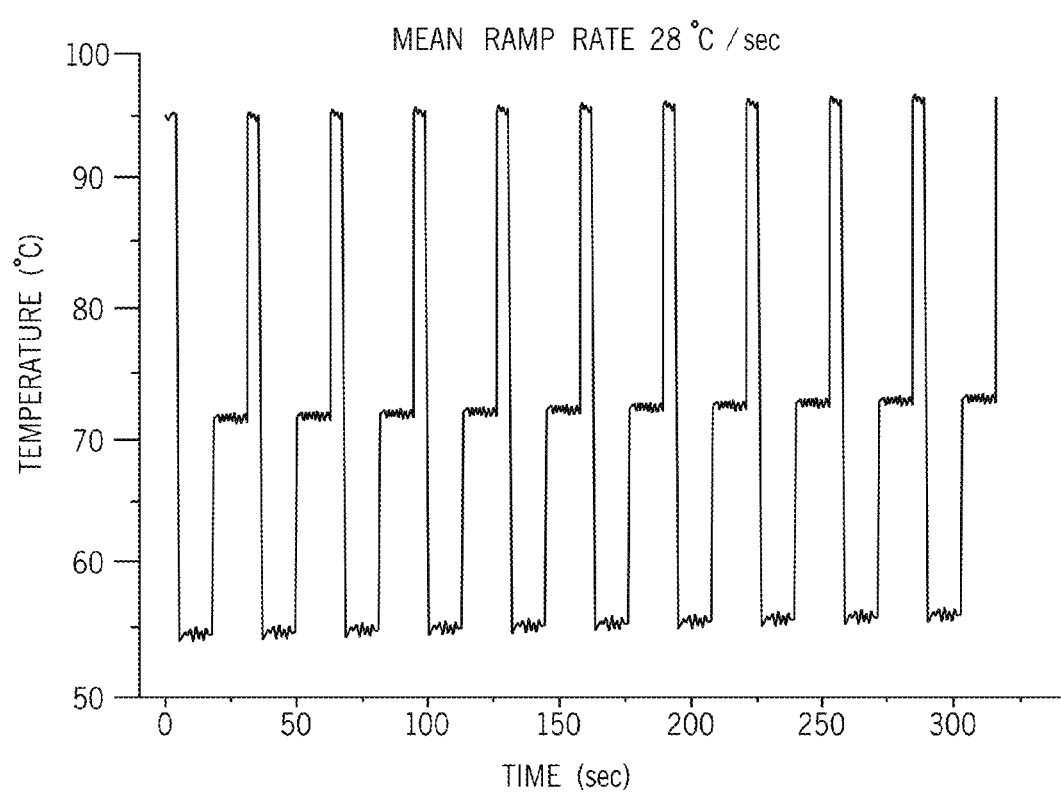
FIG. 23 depicts the thermal cycle profiles of a chip of the present invention. The mean ramp rate is about 28° C. per second.

The amplified products are detected with SYBR Green I that binds preferentially to double-stranded DNA molecules (see, FIG. 20). FIG. 21 depicts the SYBR Green staining of DNA molecules appeared at the three different thermal stages of one PCR cycle. As is shown in FIG. 21, staining of the DNA is most intense at the annealing step (e.g., at 45° C.) because most of the DNA molecules assume a double helical structure. By contrast, very little SYBR Green staining is detected at the denaturing step where the temperature is raised to e.g., 95° C. At about 72° C. where primer-directed extension is taking place, a moderate amount of staining is detected. The amount of SYBR Green stain detected throughout one complete thermal cycle is quantified as shown in FIG. 22.

The invention claimed is:

1. A method for dispensing reaction samples into micro wells in a humidified chamber at a temperature at or near the dew point comprising:
  i) providing a system comprising:
    (a) a chip for cycling at least two temperature levels, said chip comprising an array of fluidically isolated micro wells, wherein each of said micro wells is un-filled and configured for receiving a reaction sample, wherein the micro wells are coated with a hydrophobic coating suitable for the nucleic acid amplification reaction, wherein each of the micro wells has an open top surface and a closed bottom surface, wherein each micro well has a volume of approximately 0.001 µl to 10 µl, and wherein the chip is configured to be in thermal contact with a heating element;
    (b) a chamber containing ambient air; and
    (c) a dispenser located inside said chamber and configured to dispense the plurality of reaction samples separately into the fluidically isolated micro wells; and
  ii) placing said chip in said chamber and activating said system such that:
    (a) said ambient air in said chamber becomes saturated with moisture with respect to the planar surface of said chip thereby causing said chamber to become a humidified chamber, wherein the temperature inside said humidified chamber is at, or 1-5 degrees Celsius above, the dew point; and
    (b) said dispenser dispenses said plurality of reaction samples separately into said unfilled fluidically isolated microwells inside said humidified chamber.

2. The method of claim 1 wherein the chip further comprises individually controlled heating elements, each of which is operably coupled to an individual micro well of said array.

3. The method of claim 1 wherein the chip has a ramp temperature time of about 10 degrees ° C. or higher per second.

4. The method of claim 1 wherein each micro well has a volume of approximately 0.01 µl to 1 µl.

5. The method of claim 1 wherein each micro well has a volume of approximately 0.1 µl.

6. The method of claim 1 wherein the chip has a surface density of at least about 1 thermo-controllable unit per mm$^2$.

* * * * *